(12) United States Patent
Magara

(10) Patent No.: US 8,224,020 B2
(45) Date of Patent: Jul. 17, 2012

(54) APPEARANCE INSPECTION APPARATUS, APPEARANCE INSPECTION SYSTEM, AND APPEARANCE INSPECTION APPEARANCE

(75) Inventor: Takashi Magara, Kanagawa-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 904 days.

(21) Appl. No.: 12/323,268

(22) Filed: Nov. 25, 2008

(65) Prior Publication Data

US 2009/0141964 A1    Jun. 4, 2009

(30) Foreign Application Priority Data

Nov. 29, 2007  (JP) ................................ 2007-309345
Sep. 19, 2008  (JP) ................................ 2008-240777

(51) Int. Cl.
*G06K 9/00*    (2006.01)
*G06F 19/00*   (2011.01)

(52) U.S. Cl. .......................... 382/100; 382/144; 700/108

(58) Field of Classification Search .................. 382/100, 382/103, 106, 108, 141–152, 168, 181, 193–195, 382/199, 209, 219, 224, 232, 254, 274, 275, 382/276, 286–299, 305, 312, 321; 345/629, 345/7, 8; 396/50; 700/108; 250/208.1
See application file for complete search history.

(56) References Cited

U.S. PATENT DOCUMENTS

| | | | | |
|---|---|---|---|---|
| 5,917,934 A | * | 6/1999 | Chiu et al. | 382/149 |
| 6,014,524 A | * | 1/2000 | Suzuki et al. | 396/50 |
| 6,697,513 B1 | * | 2/2004 | Nakayama et al. | 382/141 |
| 6,940,527 B2 | * | 9/2005 | Hattori et al. | 345/629 |
| 6,996,447 B2 | * | 2/2006 | Onishi et al. | 700/108 |
| 7,245,273 B2 | * | 7/2007 | Eberl et al. | 345/7 |
| 7,863,552 B2 | * | 1/2011 | Cartlidge et al. | 250/208.1 |

FOREIGN PATENT DOCUMENTS

JP    2006-170622    6/2006
JP    2006-242884    9/2006

* cited by examiner

*Primary Examiner* — Seyed Azarian
(74) *Attorney, Agent, or Firm* — Finnegan, Henderson, Farabow, Garrett & Dunner, L.L.P.

(57) ABSTRACT

An appearance inspection apparatus, wherein an image inspection result based on a result of image-taking and image-analyzing a product to be inspected can be displayed with superposed on a visual field of an inspector inspecting the product to be inspected with an eye and in a position corresponding to an image in which the inspector is observing the product to be inspected is provided. An appearance inspection method includes: performing image inspection of a product to be inspected by image-taking the product to be inspected and image-analyzing the product to be inspected in an image-treating section. An inspector is capable of inspecting the product to be inspected with an eye in the state that a result of the image inspection is displayed with superposed on a visual field of an inspector inspecting the product to be inspected with an eye and in a position corresponding to an image in which the inspector is observing the product to be inspected.

17 Claims, 18 Drawing Sheets

| | LN | OP1 | OP2 | OP3 | IP | EI1 | EI1p | EI2 | EI2p | EI3 | EI3p |
|---|---|---|---|---|---|---|---|---|---|---|---|
| | Lot Number | Process 1 Operator | Process 2 Operator | Process 3 Operator | Inspector | Error 1 | Error 1 Parts | Error 2 | Error 2 Parts | Error 3 | Error 3 Parts |
| | DP0000001 | #A001 | #B001 | #C004 | #Z001 | OK | | OK | | NG | P02 |
| | DP0000002 | #A002 | #B004 | #C002 | #Z001 | OK | | OK | | OK | |
| | DP0000003 | #A001 | #B003 | #C001 | #Z002 | NG | P01 | OK | | NG | P02 |
| | DP0000004 | #A003 | #B002 | #C005 | #Z001 | OK | | OK | | OK | |
| | DP0000005 | #A002 | #B001 | #C003 | #Z003 | OK | | NG | P03 | OK | |
| | DP0000006 | #A001 | #B004 | #C001 | #Z001 | OK | | OK | | OK | |
| | DP0000007 | #A003 | #B003 | #C004 | #Z003 | NG | P02 | NG | P03 | NG | P01 |
| | DP0000008 | #A002 | #B002 | #C002 | #Z002 | OK | | OK | | OK | |

EI spans EI1, EI1p, EI2, EI2p, EI3, EI3p.

FIG. 9

APPEARANCE INSPECTION APPARATUS, APPEARANCE INSPECTION SYSTEM, AND APPEARANCE INSPECTION APPEARANCE

CROSS-REFERENCE TO RELATED APPLICATIONS

This application is based upon and claims the benefit of priority from the prior Japanese Patent Application No. 2007-309345, filed on Nov. 29, 2007 and the prior Japanese Patent Application No. 2008-240777, filed on Sep. 19, 2008; the entire contents of which are incorporated herein by reference.

BACKGROUND OF THE INVENTION

1. Field of the Invention

This invention relates to appearance inspection apparatus, appearance inspection system, and appearance inspection appearance.

2. Background Art

As appearance inspection of various products such as various electric instruments or display apparatuses or various parts used for the products, visual inspection performed with eyes by an inspector and image inspection of taking an image of a product to be inspected and image-analyzing the data thereof have been performed. In the case of the visual inspection, miss of a defect can be caused. On the other hand, in the image inspection, there is insufficiency of consistency with visual appreciation of a human, and false detection of determining a non-defective product as a defective product can be caused. Therefore, the visual inspection and image inspection are often used together.

Conventionally, the both inspections are performed independently, and the inspections cannot be performed with referring the results of both the inspections to each other, and therefore, verification of the results of both the inspections is troublesome, and as a result the accuracy of the inspections is low.

In JP-A 2006-170622 (Kokai), there has been disclosed a technique of the appearance inspection apparatus in which an image-taking device is arranged in the vicinity of the position of eye of the inspector in the visual inspection and the image of the product to be inspected in the visual inspection is taken and the data can be saved.

SUMMARY OF THE INVENTION

According to an aspect of the invention, there is provided an appearance inspection apparatus, wherein an image inspection result based on a result of image-taking and image-analyzing a product to be inspected can be displayed with superposed on a visual field of an inspector inspecting the product to be inspected with an eye and in a position corresponding to an image in which the inspector is observing the product to be inspected.

According to an aspect of the invention, there is provided an appearance inspection apparatus including: an observation-image-cognizing section for cognizing an image in which an inspector is observing an product to be inspected, including, an image-taking section for image-taking the product to be inspected, and a visual-line-detecting section for detecting a visual line of the inspector inspecting the product to be inspected with an eye; and a display in which an image inspection result based on a result of the image analysis by image-taking and image-analyzing the product to be inspected can be displayed with superposed on a visual field of the inspector and in a position corresponding to an image in which the inspector is observing the product to be inspected.

According to an aspect of the invention, there is provided an appearance inspection system including: an appearance inspection apparatus in which an image inspection result based on a result of image-taking and image-analyzing a product to be inspected can be displayed with superposed on a visual field of an inspector inspecting the product to be inspected with an eye and in a position corresponding to an image in which the inspector is observing the product to be inspected; and a data analysis section in which a result of appearance inspection of the product to be inspected by the inspector is received through a communication system from the appearance inspection apparatus and the result is analyzed.

According to an aspect of the invention, there is provided an appearance inspection method including: performing image inspection of a product to be inspected by image-taking the product to be inspected and image-analyzing the product to be inspected in an image-treating section, an inspector being capable of inspecting the product to be inspected with an eye in the state that a result of the image inspection is displayed with superposed on a visual field of an inspector inspecting the product to be inspected with an eye and in a position corresponding to an image in which the inspector is observing the product to be inspected.

BRIEF DESCRIPTION OF THE DRAWINGS

FIG. 9 is a schematic view illustrating operation of an appearance inspection apparatus according to a fifth embodiment of the invention;

DETAILED DESCRIPTION OF THE INVENTION

Hereinafter, embodiments of the invention will now be described in detail with reference to drawings.

First Embodiment

Figure 1:
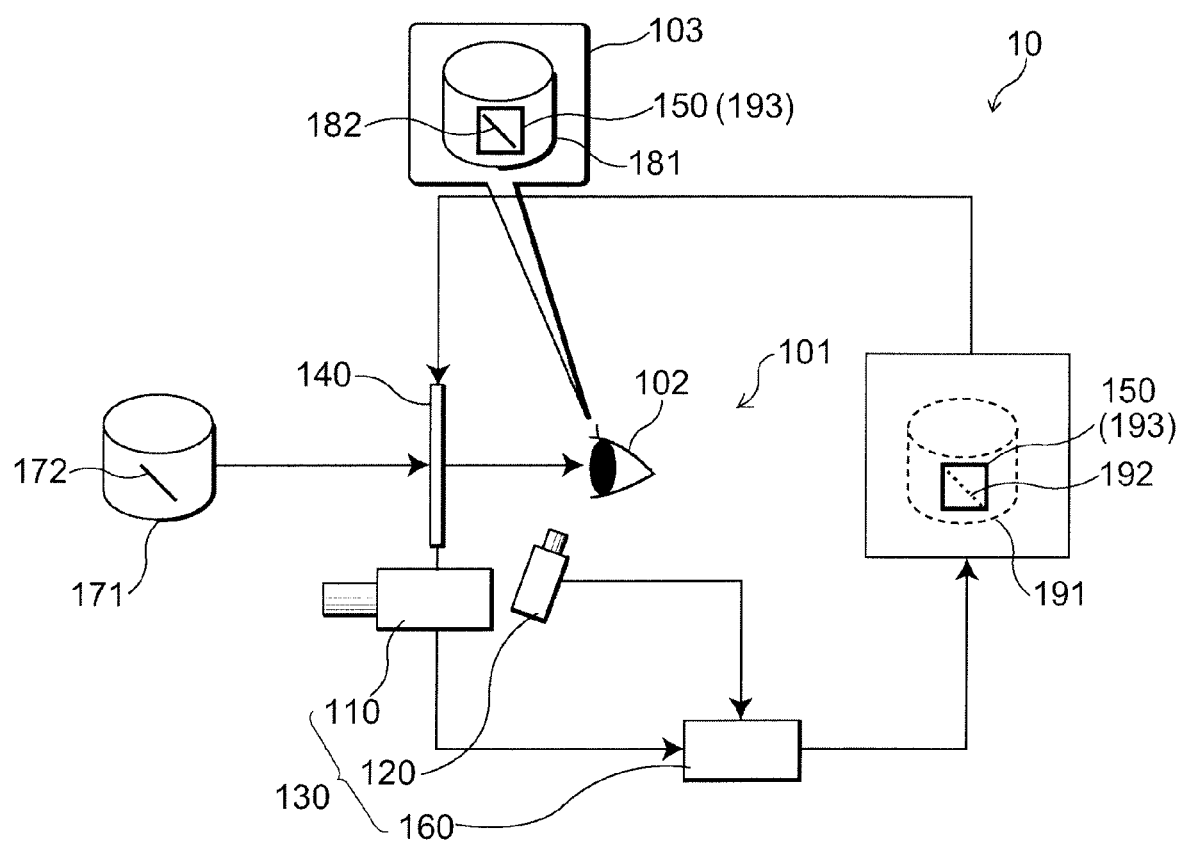
FIG. 1 is a schematic view illustrating the structure of an appearance inspection apparatus according to a first embodiment of the invention.

FIG. 1 is a schematic view illustrating the structure of an appearance inspection apparatus according to a first embodiment of the invention.

As shown in FIG. 1, an appearance inspection apparatus 10 includes, an observation-image-cognizing section 130 for cognizing an image 181 in which an inspector 101 is observing a product to be inspected 171, and a display section 140 for displaying an image inspection result 150 of the product to be inspected 171.

The observation-image-cognizing section 130 can include, an image-taking section 110 for taking an image 191 corresponding to the image 181 in which the inspector 101 is observing the product to be inspected 171, a visual-line-detecting section 120 for detecting a visual line of the inspector 101, and an image-treating section 160 for performing image treatment.

The image-taking section 110 can be composed of, for example, an image-taking device such as CCD (Charge Coupled Device), and can image-take the product to be inspected 171 with working with movement of the head of the inspector 101. This can be realized by, for example, loading and arranging the image-taking section 110 on the head of the inspector 101. And, according to need, automatic focus adjustment mechanisms or zoom mechanisms can be provided. Thereby, the image 191 corresponding to the image 181 in which the inspector 101 is observing the product to be inspected 171 can be taken. That is, for example, by complying with change of angle in observing the product to be inspected 171 or distance between the product to be observed 171 and the eye 102 of the inspector 101, the image 191 corresponding to the image 181 in which the inspector 101 is observing the product to be inspected 171 can be taken.

For the visual-line-detecting section 120, a camera for image-taking an eye 102 of the inspector 101 can be used. Moreover, a light source illuminating the eye 102 of the inspector 101 can further provided. The light source can also be omitted. And, the visual-line-detecting section 120 is arranged in front of the face of the inspector 101, and it is suitable to load and arrange the visual-line-detecting section 120 on the head of the inspector 101 so that the arrangement position can change with complying with the movement of the head of the inspector 101.

And, by the visual-line-detecting section 120, an image of the eye 102 (eyeball) of the inspector 101 is taken in, and the direction of the eye 102 (eyeball) can be obtained. This image treatment can be performed by the image-treating section 160.

Thereby, the image 181 in which the inspector 101 is observing the product to be inspected 171 can be grasped in detail. For example, when the inspector 101 observes the product to be inspected 171 by moving the visual line without moving the head, the image 181 in which the inspector 101 is observing the product to be inspected 171 can be recognized with respect to the movement of the visual line.

Based on the image 191 taken by the image-taking section 110 and the visual line detected by the visual-line-detecting section 120, the image 181 in which the inspector 101 is observing the product to be inspected 171 can be grasped by the image-treating section 160. As described above, the observation-image-cognizing section 130 can cognize the image 181 in which the inspector 101 is observing the product to be inspected 171. For example, the image 181 including the change of angle in observing the product to be inspected 171 can be cognized. Moreover, for example, the image 181 including width of the visual field when the distance between the eye 102 of the inspector 101 and the product to be inspected 171 or change of enlargement factor of the observation of the product to be inspected 171 can be cognized.

The display 140 displays the image inspection result 150 based on the result of image-taking and inspecting the product to be inspected 171. For example, the appearance of the product to be inspected 171 is image-taken by the above-described image-taking section 110, and in the image-treating section 160, the image-taken data are image-analyzed or image-cognized, and thereby, the image inspection is performed. For example, by image-analyzing the image 191 taken in the image-taking section 110 by the image-treating section 160, an image 192 of a defect is detected as an abnormal portion. Based thereon, by the image inspection, a defect 172 (such as dent and dirt) on the appearance of the product to be inspected 171. And, for the inspected a defect 172 (the image 192 of a defect), information including kind, extent, and generation place thereof can be the image inspection result 150.

On the other hand, the image taking and the inspection of the product to be inspected 171 may be performed by different apparatuses. For example, by using an image cognition system, which is not shown, the product to be inspected 171 is image-taken, and the image-taken data are image-analyzed or image-cognized, and thereby, the defect 172 on the appearance of the product to be inspected 171 can be detected. In this case, the inspection result data can be input into the image-treating section 160 by recording media, wire communication, or wireless communication.

And, the image inspection result 150 can be, for example, a frame 193 (frame-shaped figure of quadrangle or circle) or the like representing generation place of the defect.

The image inspection may be performed based on image data image-taken by another image-taking apparatus as well as the image image-taken by the above-described image-taking section 110, or the image inspection using the both thereof is possible.

And, the display 140 can display the image inspection result 150 (frame 193) with superposing the result on a visual field 103 of the inspector 101. This can be realized by, the structure of a Head Mounted Display (HMD) in which the display 140 is arranged in front of, for example, one eye of the inspector 101. Moreover, when the display 140 is a see-through type, HMD in which the display 140 is arranged in front of both eyes of the inspector 101 is also possible. Moreover, it is also possible that the display 140 is not loaded on the head of the inspector 101 but is, for example, a semi-transmissive screen provided in front of the inspector 101, and the structure can be optional as long as the display 140 can be displayed with superposed on the visual field 103 of the inspector 101.

Furthermore, the display 140 can display the image inspection result 150 (frame 193) in the position corresponding to image 181 of the observation of the inspector 101 cognized by the observation-image-cognizing section 130. That is, in the position of an image 182 of a defect that the inspector 101 is observing (position of the detected image 192 of a defect), the frame 193 corresponding to the defect is displayed. And, the display position of the image inspection result 150 (frame 193) can be changed according to the change of the image 181 (image 182 of a defect) of observation changing with corresponding to change of position of the head or visual line of the inspector 101.

Thereby, the inspector 101 can see the image inspection result 150 (frame 193) at the same time, with superposing the result on the visual field 103 seeing the product to be inspected 171. When the inspector 101 moves the head or moves the visual line, the display position of the image inspection result is changed, complying with the movement, and the frame 193 representing the position of a defect can be constantly displayed in the position of a defect appearing in the observation image.

Thereby, the inspector 101 can easily refer the image inspection result with performing visual inspection, and appearance inspection of high accuracy can be performed with high efficiency.

The display position of the image inspection result 150 can be controlled by the image 181 of the observation cognized based on the visual line detected and the image 191 taken by the image-taking section 110, in the image-treating section 160.

Moreover, the image-treating section 160 can have a function of performing image inspection by performing image treatment based on the image-taken data image-taken by the image-taking section 110 or another image-taking apparatus.

As described above, the example in which the image inspection result 150 is displayed as the frame 193 is presented, but the present invention is not limited thereto. The result can be displayed by various figures or letters such as various line, triangle, quadrangle, polygon, circle, ellipse, arrow, cross bar, double cross, according to kind, extent, generation place of the defect. Moreover, line type, hatching, color, blink, or the like thereof can be changed. Moreover, hearing sense may be used as well as acting on visual sense, for example, sound is generated when a heavy defect is generated.

First Example

Hereinafter, the embodiment will be explained in detail by a first example.

FIG. 2 are schematic views illustrating the structure of an appearance inspection apparatus according to a first example of the invention.

Figure 2A:
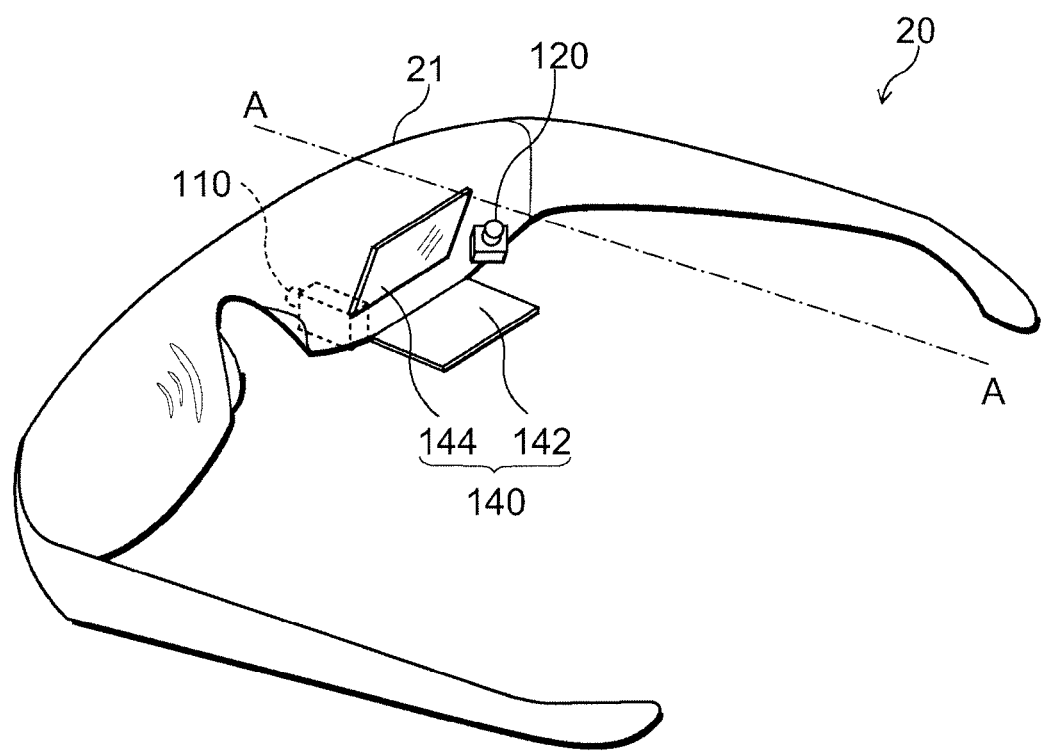
FIGS. 2A and 2B are schematic views illustrating the structure of an appearance inspection apparatus according to a first example of the invention.
Figure 2B:
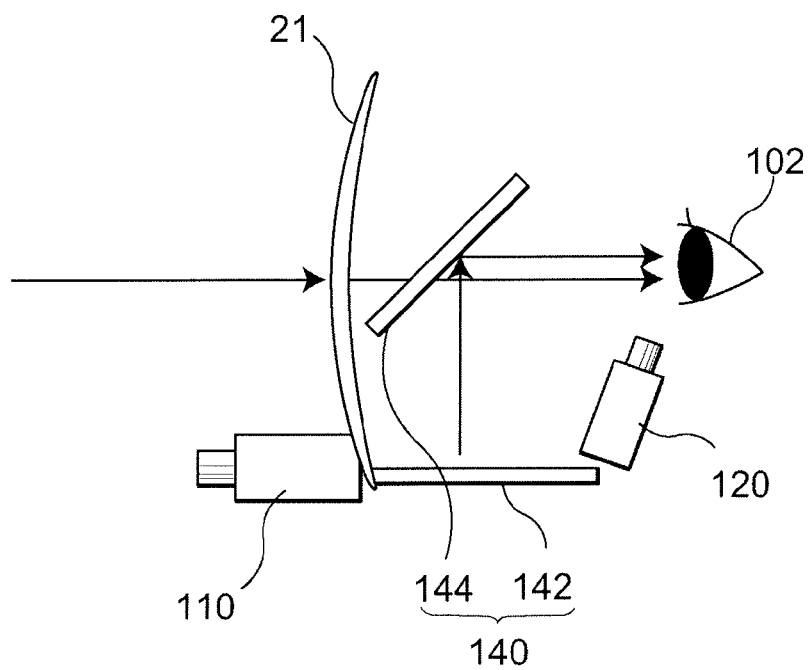

FIG. 2A is a perspective view showing the structure of the appearance inspection apparatus 20 according to the first example, and the FIG. 2B is a sectional view of the A-A line section. With respect to each of the figures after FIG. 2, the same signs are appended to the same components as described above for a previously presented figure, and the detailed explanation will be appropriately omitted.

As shown in FIGS. 2A and 2B, the appearance inspection apparatus 20 of the first example has the image-taking section 110, and the visual-line-detecting section 120, and the display 140. And, they are integrated as the structure of HMD type to be loaded on the head of the inspector 101. In this figure, the image-treating section 160 is omitted.

The image-taking section 110 includes an image-taking device composed of CCD provided in the lower position of glasses 21, and takes the image of the product to be inspected 171 with working with the movement of the head of the inspector 101.

The visual-line-detecting section 120 includes a camera provided in the lower of the glasses 21. Thereby, the direction of a pupil of the eye 102 is grasped to detect the visual line of the inspector 101.

The display 140 includes, a small liquid crystal panel 142 provided in the lower part of the glasses, and a half mirror 144 forming an image by reflecting a projection light from the liquid crystal panel. Thereby, the inspector 101 can perform the observation by superposing the image inspection result 150 and the image of the product to be inspected 171 in the visual field at the same time.

Thereby, inspector 101 can easily refer the image inspection result with performing the visual inspection, and the appearance inspection of high accuracy can be performed with high efficiency.

Hereinafter, the state of the appearance inspection using the appearance inspection apparatus 20 of the first example will be explained. In this example, a portable phone is inspected as the product to be inspected 171, dent, dint, or dirt on the surface of the portable phone is detected as the defect.

FIGS. 3A to 3F are schematic view illustrating the display of the appearance inspection apparatus according to the first example of the invention.

FIGS. 3A to 3F are states of the visual field 103 of the inspector 101. The pictures (210a to 210f) of the portable phone 210 in the figures are images 181 observed by the inspector 101. Moreover, quadrangular frames 211 to 213 in the figures illustrate the image inspection results 150 displayed so as to be supposed on the visual field 103. The inspector 101 is seeing these images superposed at the same time.

Figure 3A:
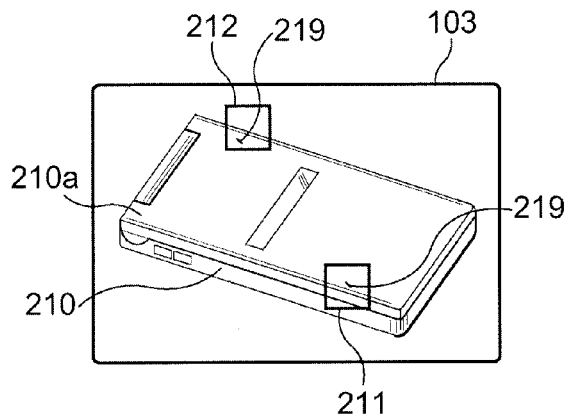
FIGS. 3A to 3F are schematic views illustrating the display of the appearance inspection apparatus according to the first example of the invention.
Figure 3B:
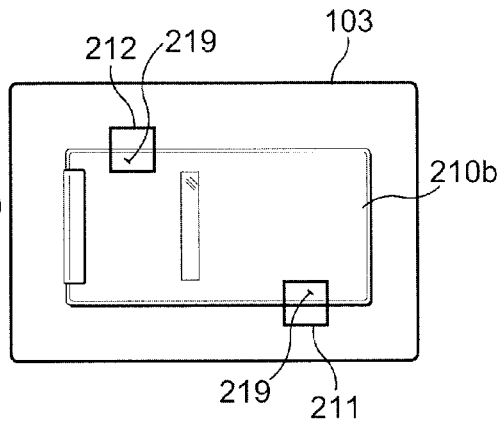
Figure 3C:
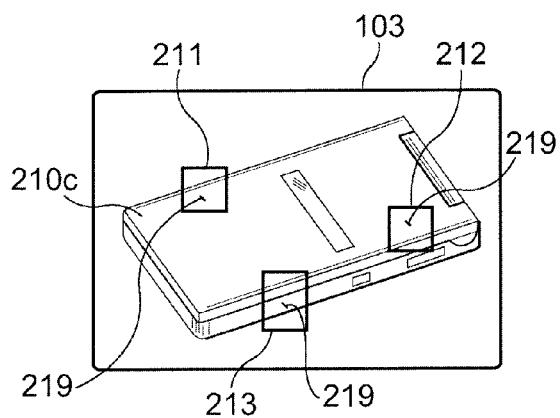
Figure 3D:
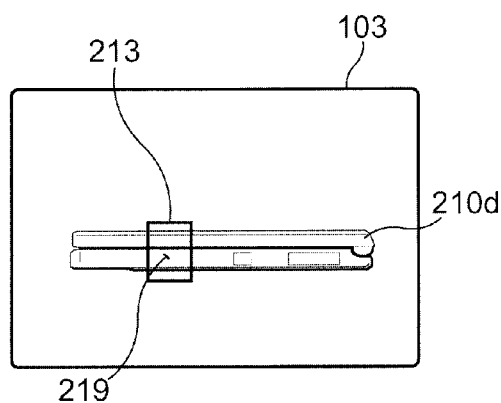
Figure 3E:
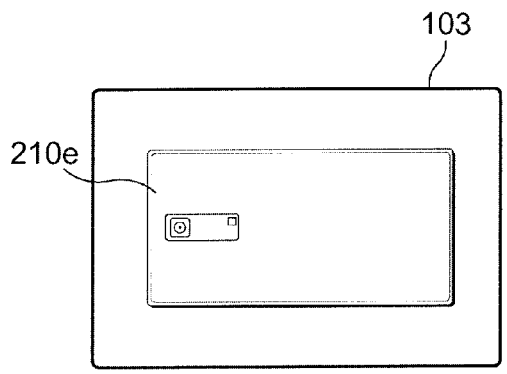

As shown in FIG. 3A, for inspecting the portable phone 210 that is the product to be inspected, for example, the inspector observes the portable phone 210 from the diagonal direction. In this time, the image 210a is being observed from the diagonal direction of the portable phone 210. And, the appearance of the portable phone 210 is image-taken by the image-taking section 110 and image-treated, and as a result of the image inspection, the dent 219 on the surface of the portable phone is detected. As the image inspection result 150, the frames 211, 212 representing the generation position of the defects are being displayed with corresponding to the taken-image 210a.

Furthermore, when the inspector 101 picks up the portable phone 210 or moves the position of the head to the portable phone 210 and thereby performs the inspection with viewing the portable phone 210 from various directions, as shown in FIGS. 3B to 3E, the images 210b to 210e in viewing the portable phone 210 are changed. And, the appearance inspection apparatus 20 of this example can change the display of the frames 211 to 213 that are the image inspection results 150 by changing the position of the display according to the change of the images 210b to 210e.

Figure 3F:
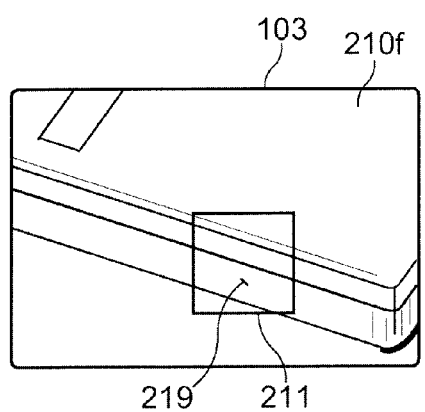

FIG. 3F illustrates an observation image in the case that the portable phone 210 is viewed nearly with reducing the distance between the portable phone 210 and the eye 102 of the inspector 101. As shown in FIG. 3F, the inspector 101 views the portable phone (the product to be inspected) 210 nearly, and thereby, the image of the portable phone (the product to be inspected) 210 is enlarged. And, according to the enlargement, display position of the image inspection result 150 (frame 211) is changed.

As described above, the appearance inspection apparatus 20 of this example can display the image detection result 150 in the position corresponding to the images, according to the angle or enlargement ratio or reduction ratio of the image when the inspector 101 observes the product to be inspected 171.

Thereby, the inspector 101 can easily refer the image inspection result 150 with performing the visual inspection. And, the inspection 101 can not only inspect the entirety of the appearance of the portable phone 210 cyclopaedically but also heavily inspect the parts of the frames 211 to 213 displayed as the image inspection result. Thereby, miss of a defect can be prevented, and heavy visual inspection can be performed. Thereby, the inspection of high accuracy can be performed with high efficiency.

In the inspection method in which the determination level of the defect detection of the image inspection is strictly set and the product to be inspected determined as a defective product by the image inspection is finally determined in the practical view point by the visual inspection, the appearance inspection apparatus 20 of this example can be very efficiently utilized.

In the appearance inspection apparatus 20 of this example, the image 181 being observed by the inspector 101 (image 191) may be displayed on the display apparatus provided separately. Thereby, the image 181 (image 191) being observed by the inspector 101 can be viewed by another person except for the inspector 101, and for example, this can be utilized for training or technique instruction of inspectors.

Second Embodiment

Next, the second embodiment of the invention will be explained. In the appearance inspection apparatus of this embodiment, a visual-inspection-result-inputting section for inputting a result of the visual inspection by the inspector 101 is further provided.

Figure 4:
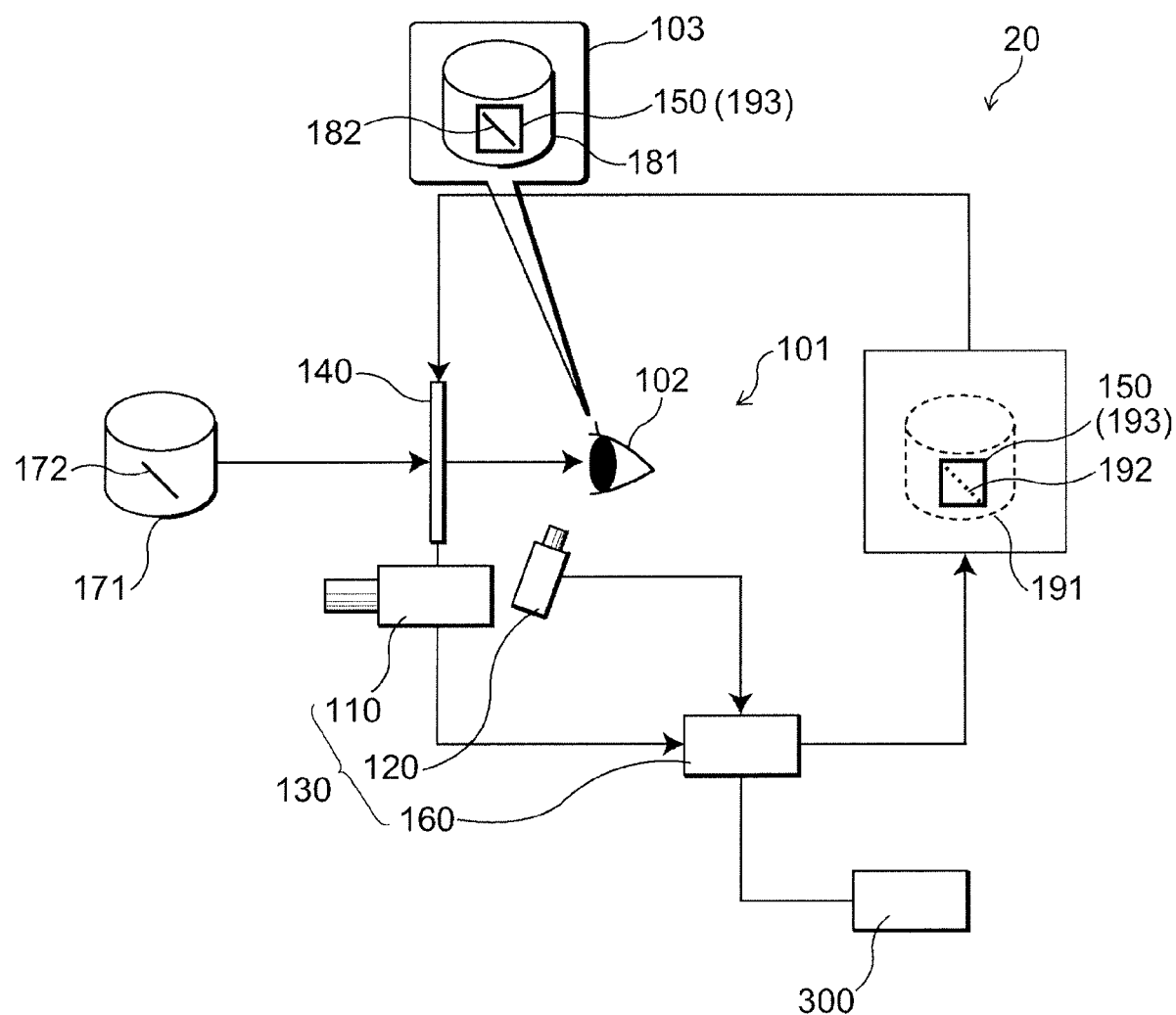
FIG. 4 is a schematic view illustrating the structure of an appearance inspection apparatus according to a second embodiment of the invention.

FIG. 4 is a schematic view illustrating the structure of the appearance inspection apparatus according to the second embodiment of the invention. As shown in FIG. 4, with respect to the appearance inspection apparatus 10 illustrated in FIG. 1, the appearance inspection apparatus 20 of this embodiment further includes a visual-inspection-result input section 300 for inputting the result of the visual inspection by the inspector 101.

For the visual-inspection-result input section 300, the input devices having various structures such as button, keyboard, touch panel, foot switch, voice-input device, and visual-line-input device can be used. And, for example, in the appearance inspection illustrated in FIG. 3, with respect to the frames 211 to 213 representing the image inspection results, the inspector 101 can easily input the respective inspection results (acceptance or rejection or the like). Thereby, the efficiency and accuracy of the appearance inspection can be improved.

Third Embodiment

Next, a third embodiment of the invention will be explained.

Figure 5:
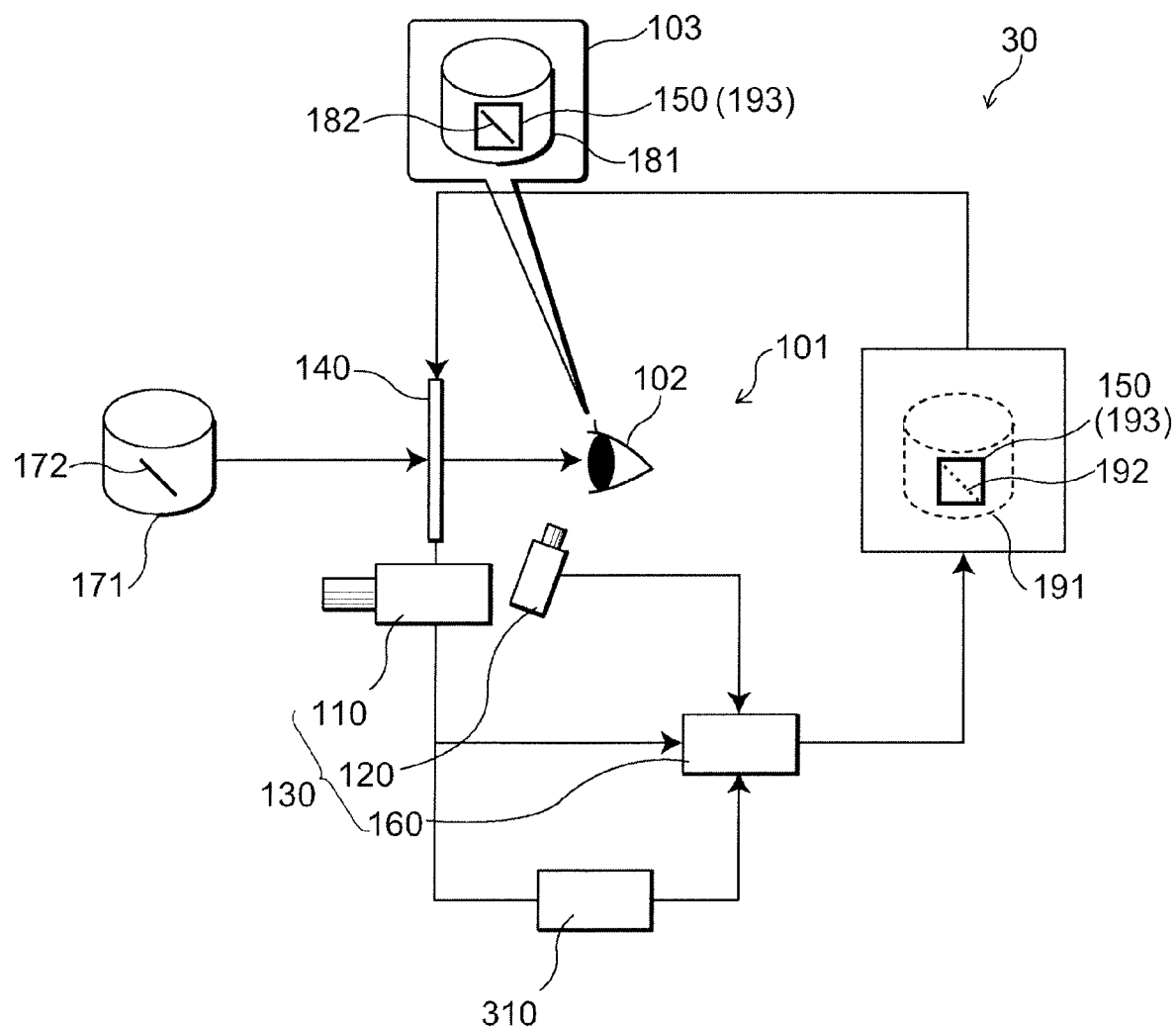
FIG. 5 is a schematic view illustrating the structure of an appearance inspection apparatus according to a third embodiment of the invention.

FIG. 5 is a schematic view illustrating the structure of the appearance inspection apparatus according to the third embodiment of the invention. As shown in FIG. 5, with respect to the appearance inspection apparatus 10 illustrated in FIG. 1, the appearance inspection apparatus 30 of this embodiment further includes an image-inspection-treating section 310. That is, in the appearance inspection apparatus 10 illustrated in FIG. 1, the image-treating section 160 is designed so as to perform both of the image treatment for cognizing the image 181 in which the inspector 101 observes the product to be inspected 171 and the image treatment for image inspection of the product to be inspected 171, but in the appearance inspection apparatus 30 of the third embodiment, these functions are separated.

That is, the image-treating section 160 performs the image treatment for cognizing the image 181 in which the inspector 101 observes the product to be inspected 171. And, the image inspection treating section 310 carries out the image treatment for the image inspection based on the image obtained in the image-taken section 110. As described above, the image treatment for cognizing the image 181 observed and the image treatment for image inspection are carried out separately in the image-treating section 160 and the image-inspection-treating section 310, respectively, and thereby, the treatments can be performed at a high speed, and as a result, the appearance inspection of high accuracy can be performed with high efficiency.

In the appearance inspection 30 illustrated in FIG. 5, the visual-inspection-result-inputting section illustrated in FIG. 4 may be further provided.

Fourth Embodiment

As described above, for the image data to be an origin of the image inspection, the case that the image date is image-taken in the image-taking section 110 is presented, but the image date is not limited thereto, and it is also possible that the product to be inspected is image-taken by another image-taking apparatus and the image inspection result 150 is obtained from the data thereof and the image inspection result 150 is displayed with corresponding to the image 181 observed by the inspector 101.

Figure 6:
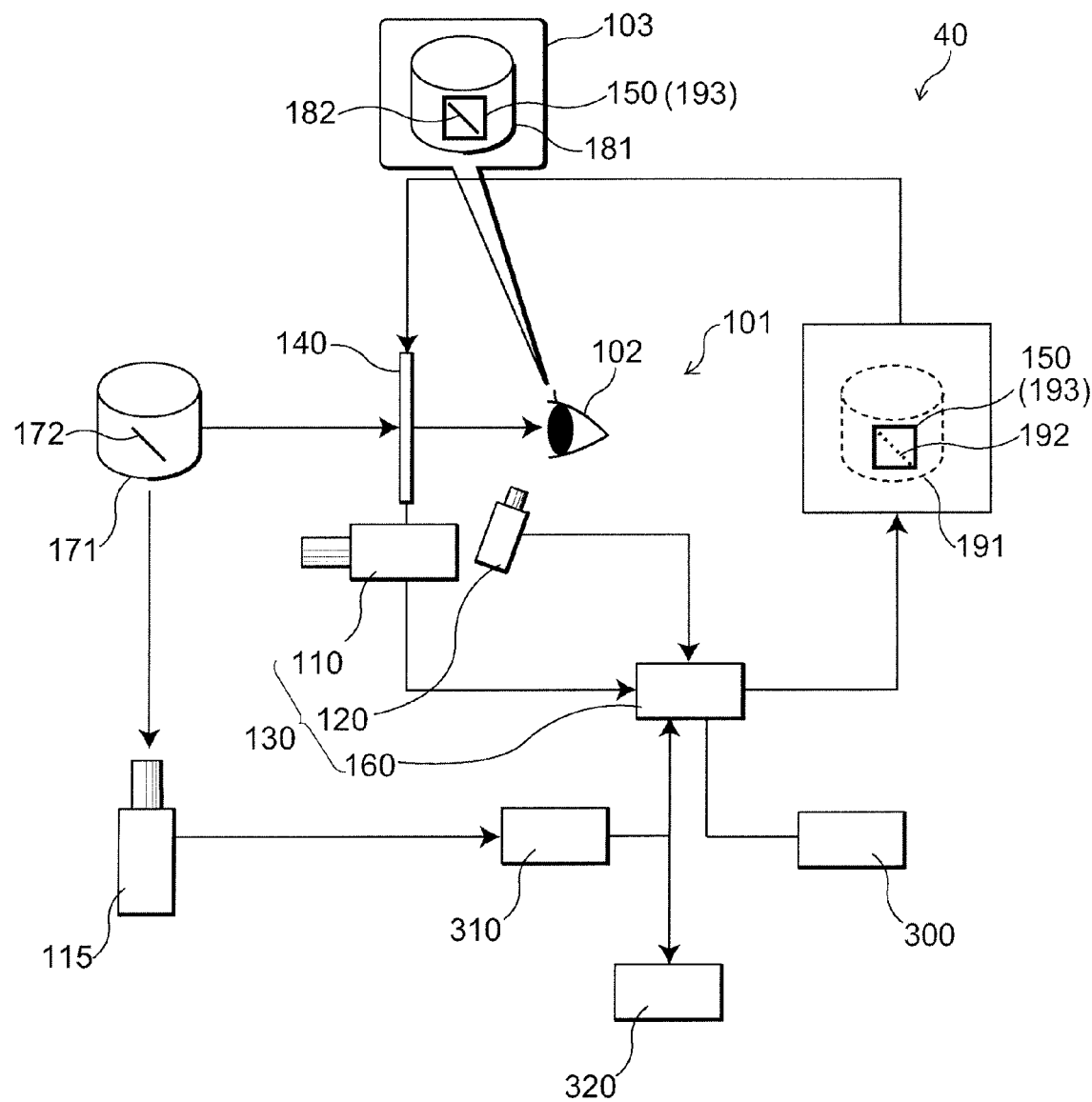
FIG. 6 is a schematic view illustrating the structure of an appearance inspection apparatus according to a fourth embodiment of the invention.

FIG. 6 is a schematic view illustrating the structure of the appearance inspection apparatus according to the fourth embodiment of the invention. As shown in FIG. 6, with respect to the appearance inspection apparatus 30 illustrated in FIG. 5, the appearance inspection apparatus 40 of this embodiment further includes an image-taking apparatus 115 for image-taking appearance of the product to be inspected 171. The image data of the product to be inspected 171 image-taken in the image-taking apparatus 115 is image-treated by the image inspection-treating section 310, and thereby the defects are detected.

Thereby, the image inspection can be carried out independently from the visual inspection. For example, (a plurality of) image-taking apparatus(es) 115 are provided in a predetermined places of the production line, and for example, the method for image-inspecting the appearance such as front face, back face, side face of the product to be inspected on line and the visual inspection can be combined. Thereby, (a part of) the image inspection can be carried out independently from the visual inspection, and the appearance inspection of high accuracy can be performed with high efficiency.

As shown in FIG. 6, the visual-inspection-result-inputting section 300 illustrated in FIG. 4 may be further provided.

Moreover, as shown in FIG. 6, an inspection data storage section 320 for storing and outputting the data of the image inspection result by the image-taking apparatus 115 or date of the visual inspection result may be further provided.

Second Example

FIGS. 7A to 7E are schematic views illustrating the display of an appearance inspection apparatus according to a second example of the invention.

FIGS. 7A to 7E illustrate the display observed by the inspector 101 in the case of performing the appearance inspection by using the appearance inspection apparatus 40 illustrated in FIG. 6. In this case, before the inspector 101 performs the visual inspection, the appearance of the portable phone 210 that is product to be inspected 171 is inspected in the image-taking apparatus 115 provided separately.

Figure 7A:
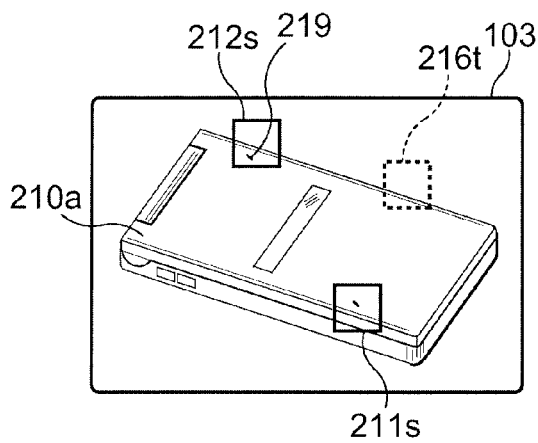
FIGS. 7A to 7E are schematic views illustrating the display of an appearance inspection apparatus according to a second example of the invention.
Figure 7B:
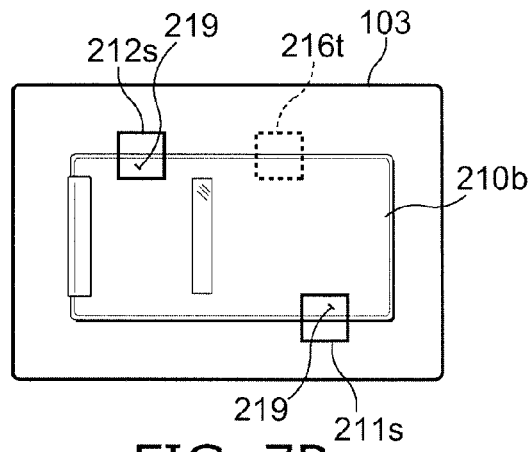
Figure 7C:
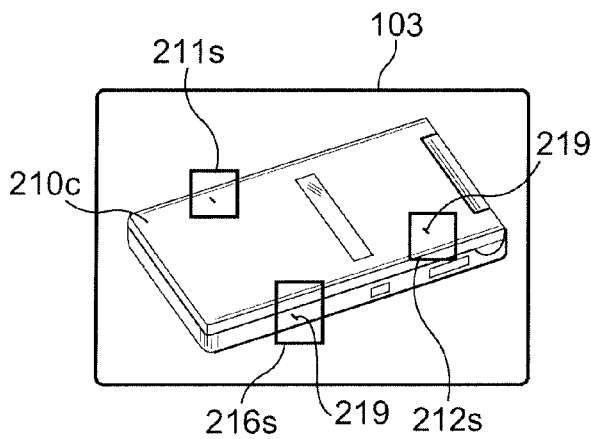
Figure 7D:
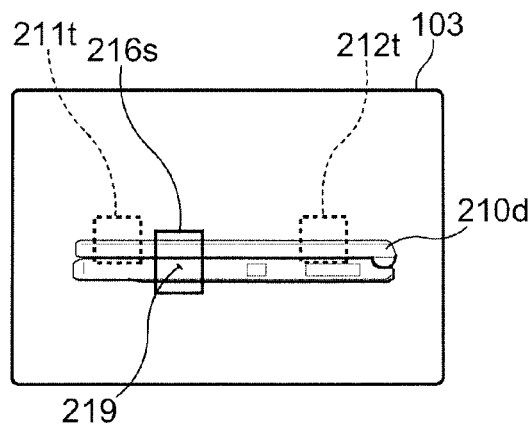
Figure 7E:
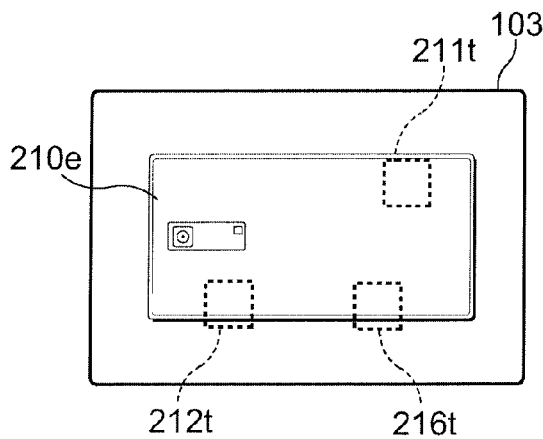

As shown in FIG. 7A, in the visual field of the inspector 101, the image inspection results 150 are displayed by solid line frames 211s and 212s and a dot line frame 216t with corresponding to the image 210a of observation (observation from the diagonal direction in this case) of the portable phone 210. That is, in this example, when there is a defect in the region the inspector 101 can see, the existence is represented by the solid line frames 211s and 212s, and when there is a defect in the region inspector 101 cannot see, the existence is represented by the dot line frame 216t.

And, when the inspector 101 performs the inspection by viewing the portable phone 210 from various directions, as shown in FIGS. 7B to 7E, the position of the display of the frame representing the defect detected by the image inspection is changed according to the images 210b to 210e of the observation in viewing the portable phone 210, and the display can be performed by changing the line type of the frame according to whether the defect can be observed. For example, in FIG. 7B, the defect existing in the region that cannot be seen is represented by the dot line frame 216t. Moreover, in FIG. 7C, because all of the three defects can be seen, all of the frames representing the defects are displayed as solid frames 211s, 212s, and 216s. Moreover, in FIG. 7D, the defect in the region that cannot be seen is displayed as dot line frames 211t, 212t. Moreover, in FIG. 7E, because all of the defects cannot be seen from this observation direction, the positions of the defects are displayed as the dot lines 211t, 212t, and 216t.

As described above, in the appearance inspection apparatus of this example, the display can be performed by changing the type of display of the image inspection result according to whether the defect can be seen from the visual field of the inspector 101, and the image inspection result can be easily referred with performing the visual inspection, and the appearance inspection of high accuracy can be performed with high efficiency.

In the above, the image inspection result can be displayed by various methods such as changing of color of the display or blinking, as well as the solid line and dot line.

Moreover, in the above example, the example in which the image inspection is performed based on the image obtained by another image-taking apparatus 115 has been explained, but the present invention is not limited thereto, and also in the case of performing the image inspection based on the image-taken data obtained by the image-taking section 110, the display contents (line type or color or the like of the frame) of the image inspection result 150 can be changed according to whether the defect is in the visual field of the inspector 101. In this case, the inspection data storage section 320 for storing the inspection result based on the image-taken data obtained in the image-taking section 110 is provided and this can be utilized. Thereby, the data of the image inspection result is stored separately from the visual field of the inspector 101 changing constantly, and can be used for the display.

Third Example

FIGS. 8A to 8F are schematic views illustrating the display of an appearance inspection apparatus according to a third example of the invention.

In the third example, the display of the image inspection result according to the implementation state of the visual inspection of the inspector 101 is illustratively changed.

Moreover, in this example, the case that the product to be inspected is a personal computer (PC) will be exemplified. And, in this example, as the appearance inspection of PC, dent, dint, dirt, and so forth of the surface thereof are inspected as the defects.

FIGS. 8A to 8F show states of the visual field 103 of the inspector 101, and illustrate the image inspection result 150 displayed with superposed on the visual field 103 by images 220a to 220f of a PC 220 which the inspector 101 observes and the appearance inspection apparatus of the example of the invention. Moreover, in this example, the image inspection is performed based on the image taken by the image-taking section 110, but may be performed based on the image taken by the another image-taking apparatus 115. And, in this example, the inspection of the inspector 101 is performed in order of FIG. 8A to 8F.

Figure 8A:
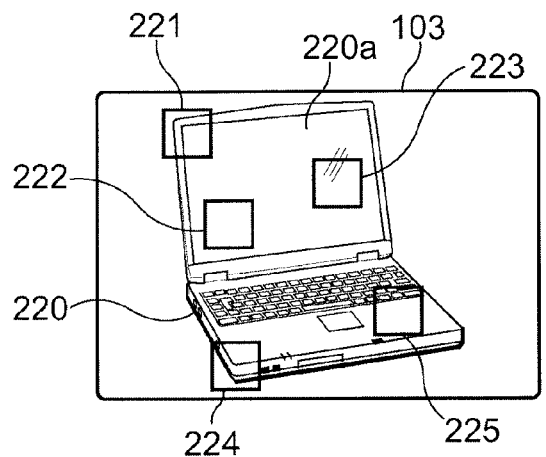
FIGS. 8A to 8F are schematic views illustrating the display of an appearance inspection apparatus according to a third example of the invention.

As shown in FIG. 8A, the image inspection result 150 is displayed by the frames 221 to 225 with corresponding to the image 220a in which the inspector 101 is observing the PC 220. Thereby, the inspector 101 can grasp all of the positions of the five defects to be detected from this direction.

And, the inspector 101 sequentially performs the appearance inspection in frames 221 to 225 determined as defects by the image inspection.

Figure 8B:
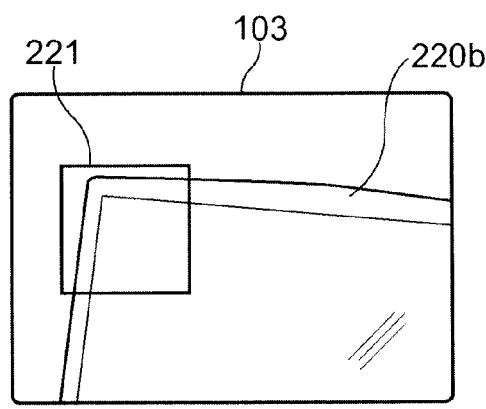

For example, the appearance inspection is performed from the frame 221. In this time, the inspector 101 inspects the appearance of PC 220 in the frame 221 with approximating the face to a part of the frame 221 of PC 220 that is the product to be inspected 171. In this case, as shown in FIG. 8B, the part of the frame 221 in an image 220b of PC 220 is magnified. And, the display position of the frame 221 also changes according to the image 220b. And, whether the defect displayed by the frame 221 is non-defective or defective is determined. In this time, the inspector 101 gazes at the inside of the frame 221 for a certain time, for example, several seconds. The time of the gaze can be detected by detecting the visual line of the inspector 101 by the visual line detection section 120. And, observation of the inside of the display (frame) of the image inspection result 150 for a certain time or more can be assumed as the implementation of the visual inspection. Thereby, the implementation, non-implementation, or implementation end of the visual inspection by the inspector 101 can be determined.

That is, in the appearance inspection apparatus of this example, whether the place determined as a defect by the image inspection result is subjected to the visual inspection can be grasped, and if required visual inspection is not performed, this can be informed by alarm sound or the like. Thereby, inspection miss by the inspector 101 can be defeated. By the contents of the image inspection result (type, extent, and so forth of the result), whether the detection or supervision of whether the detector 101 has visually inspected (gazed at) the above-described display (frame) of the image inspection result is performed or not can also be changed. Moreover, by the contents of the image inspection result (type, extent, and so forth of the result), the determination criteria of the gaze time can be appropriately set.

Figure 8C:
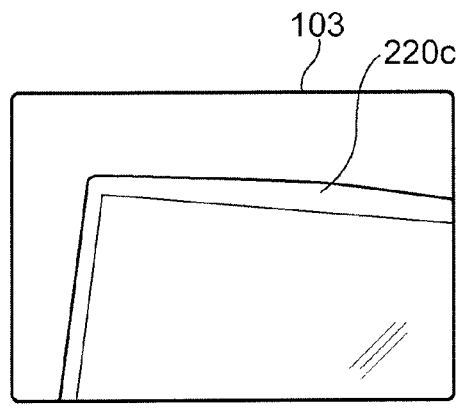

Furthermore, by the visual inspection, after the inspection of the inside of the predetermined frame is finished (gaze of the frame inside for the certain time is finished), this frame can be, for example, vanished. FIG. 8C represents the state in which the frames of display of the defects of which the inspection has been finished (the gaze has been finished) are vanished (the frames 221 in the FIG. 8B has disappeared). That is, by detecting the direction or movement of the eye 102 of the inspector 101, the display contents can be modified so that the detection thereof is used as a trigger.

Thereby, the inspector 101 can perform the visual inspection without inspecting the same place of a defect repeatedly and without miss of the inspection place.

In the above, the example in which the frame is vanished in the finish of the visual inspection has been presented, but the invention is not limited thereto, and by various methods, the finish of the visual inspection can be indicated. For example, various methods for changing shape or color of the frame that is display representing the position of the defect, line type (such as dot line and solid line) of the frame, blinking of the frame, or the like can be applied. Moreover, separately from the frame representing the position of the defect, digits or figures representing the number of the defects detected in the image inspection, the number of the finished inspection thereof and the residual number thereof may be used.

Figure 8D:
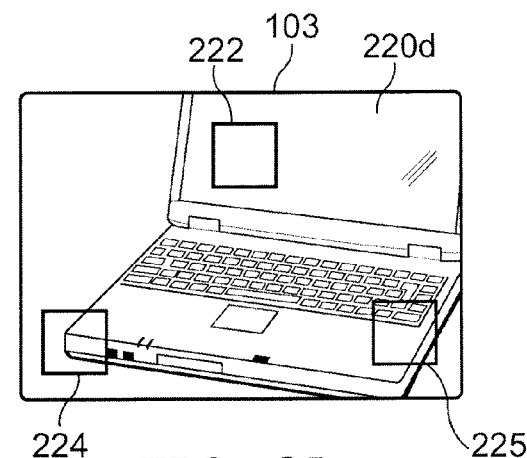
Figure 8E:
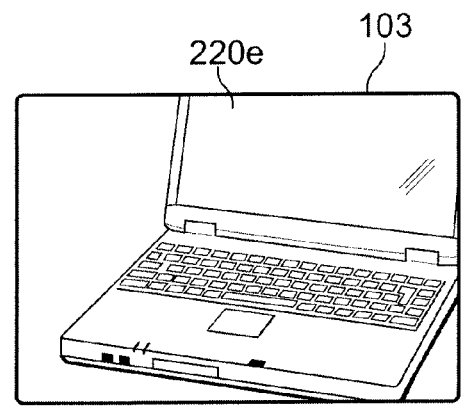

Subsequently, the visual inspection is performed from another observation angle in the same manner, and the visual inspection of frames 222, 224, and 225 is performed as shown in FIG. 8D. And, after the finish thereof, as shown in FIG. 8E, these frames 222, 224 and 225 representing defects disappear (the display is modified). And, then, similarly, the visual inspection about a frame 223 is performed, and finished (not shown).

Figure 8F:
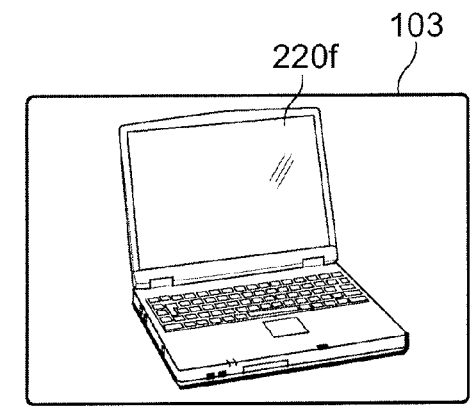

And, as shown in FIG. 8F, in this state, all of the display (frames 221 to 225) of the defects represented by the FIG. 8A disappears (is modified), and thereby, the inspection of this state (the state in which the screen of PC and the keyboard are opened) is finished. Moreover, subsequently, the appearance inspection and so forth in the state that the screen and the keyboard of PC are closed are performed in the same manner.

In the screen in which the visual inspection of all of the defects is finished as illustrated in FIG. 8F, display of message, lighting of lamp, generation of sound or the like for informing the finish of the visual inspection may be performed.

As described above, in the appearance inspection apparatus of this example, the display of the image inspection result 150 is changed based on the time in which the inspector 101 gazes at the inspection part of the product to be inspected 171, and therefore, the inspector 101 can perform the visual inspection without inspecting the same place of a defect repeatedly and without miss of the inspection place, and therewith, can refer the image inspection result easily and with good efficiency, and the appearance inspection of high accuracy can be performed with high efficiency.

In the above, the visual-inspection-result-inputting section 300 may be provided and the result of the visual inspection by the inspector 101 may be input therein. For example, by detecting the finish of the visual inspection of the frame 221 representing the image inspection result by the above-described gaze time, at the time, the inspector 101 can input the result of the gaze inspection (acceptance or rejection) when the display of the frame 221 disappears (the display changes). Thereby, the efficiency of the visual inspection can be enhanced. For the visual-inspection-result-inputting section 300, the input devices having various structures such as button, keyboard, touch panel, foot switch, voice-input device, and visual-line-input device can be used.

Moreover, if a defect having not been detected in the image inspection is detected with eyes, display of another frame or the like other than the frame 193 representing the image inspection result 150 may be performed at the place corresponding thereto. Thereby, the difference between the image inspection and the visual inspection is displayed and this can be utilized for improvement of the inspection accuracy. Moreover, the data of the difference can also be saved.

Furthermore, the apparatus is composed so that the data of whether the result of the visual inspection is acceptance or rejection with respect to each of, for example, the frames 193 representing the image inspection results 150 is accumulated and so that the determination criteria of the image inspection is automatically adjusted, and thereby, a learning function can be provided for the image inspection, and efficiency and accuracy of the appearance inspection can be improved. That is, in the appearance inspection apparatus of this example, the image inspection result 150 and the visual inspection result can be easily referred to each other, and the above-described leaning function can be easily provided for the image inspection, and this becomes a large advantage.

In the appearance inspection apparatus of the embodiment of the invention, for performing adjustment so that the image 191 taken by the image-taking section 110 accords with the image 181 of observation by the inspector 101, a function in which a profile or the like of the shape produced based on the image 191 taken in the image-taking section 110 or the taken image 191 is displayed in the display 140 may be provided.

Fifth Embodiment

The structure of an appearance inspection apparatus according to a fifth embodiment of the invention is the same as the appearance inspection apparatus according to the fourth embodiment. However, this embodiment has characteristics that the inspection data in the inspection data storage section 320 is stored in associate with the information specifying the product to be inspected 171. As the information specifying the product to be inspected 171, for example, the data for the production number or type or the like of the product to be inspected 171 or the data such as lot number can be used. For example, according to the product to be inspected 171, the data such as the production time are possible. Hereinafter as the information specifying the product to be inspected 171, the example in which the lot number is used will be explained.

FIG. 9 is a schematic view illustrating the operation of the appearance inspection apparatus according to the fifth embodiment of the invention. That is, this figure illustrates a state of the inspection data in the inspection data storage section 320 of the appearance inspection apparatus.

As shown in FIG. 9, in the inspection data storage section 320, in association with each of lot numbers LN, the data of the appearance inspection apparatus of "Error 1" EI1, "Error 2" EI2, and "Error 3" EI3 that are error items (error categories) EI are stored. In this case, in a data format of a tabular form, existence or non-existence of each of errors is stored as the data in the places of squares of the table corresponding to the respective lot numbers so as to be represented by display of "NG" or "OK".

For example, "Error 1" EI1 represents "scratch", and "Error 2" EI2 represents "dint", and "Error 3" EI3 represents "dirt". And, the data for parts in which each of the error items is generated are registered together. For example, the parts are "P01", "P02", "P03", and the data for the parts which corresponds to each of the error items and in which the errors are generated are stored in the columns of "Error 1 parts" EI1p, "Error 2 parts" EI2p, and "Error 3 parts" EI3p with corresponding to the lot numbers LN.

Furthermore, not only the data of the appearance inspection by the inspector 101 but also the data of the image inspection result based on the image obtained by the image-taking apparatus 115 or the image obtained by the image-taking section 110 may be stored in association with the lot numbers.

Furthermore, in this specific example, information for an operator OP 1 of step 1, an operator OP 2 of step 2, an operator OP 3 of step 3, and an inspector IP 101 is stored with corresponding to each of the lot numbers. The inspector IP may be the inspector for the appearance inspection. Furthermore, various data such as material, parts, type of the processing equipment, and time of production according to the production of the product to be inspected 171 may be stored in association with the lot numbers.

As described above, in the appearance inspection apparatus according to this embodiment, in the inspection data storage section 320, the results of the appearance inspection is stored in association with the lot of the product to be inspected 171. Furthermore, various data in the production process of the product to be inspected 171 may be stored in association with the lot. Thereby, the labor hour for reference of the appearance inspection result can be saved, and the analysis of the appearance inspection result can be performed efficiently. And, the efficiency of the error factor analysis can be improved.

As described above, the inspection data storage section 320 stores the data of the image inspection result based on the image obtained in the image-taking apparatus 115 or the image obtained by the image-taking section 110 or the data of visual inspection result and outputs the data.

At this time, the storage of the data to the inspection data storage section 320 can be composed so that the data are automatically stored into the inspection data storage section 320 from the output of the image-inspection-treating section 310 or the image-treating section 160. Moreover, for the result of the appearance inspection of the inspector 101, for example, in the case of the visual line input, the data is automatically input into the inspection data storage section 320 from the image-treating section 160, and for example, in the case of the input by using the visual-inspection-result inputting section 300, the data can be automatically input into the inspection data storage section 320 from the visual-inspection-result inputting section 300.

That is, the inspection data storage section 320 automatically collects and stores the result of the appearance inspection.

Thereby, the image inspection result or the result of the appearance inspection that is mainly input by human can be automatically input into the inspection data storage section 320, and the operation relating to the appearance inspection can be made to be more efficient.

Sixth Embodiment

Figure 10:
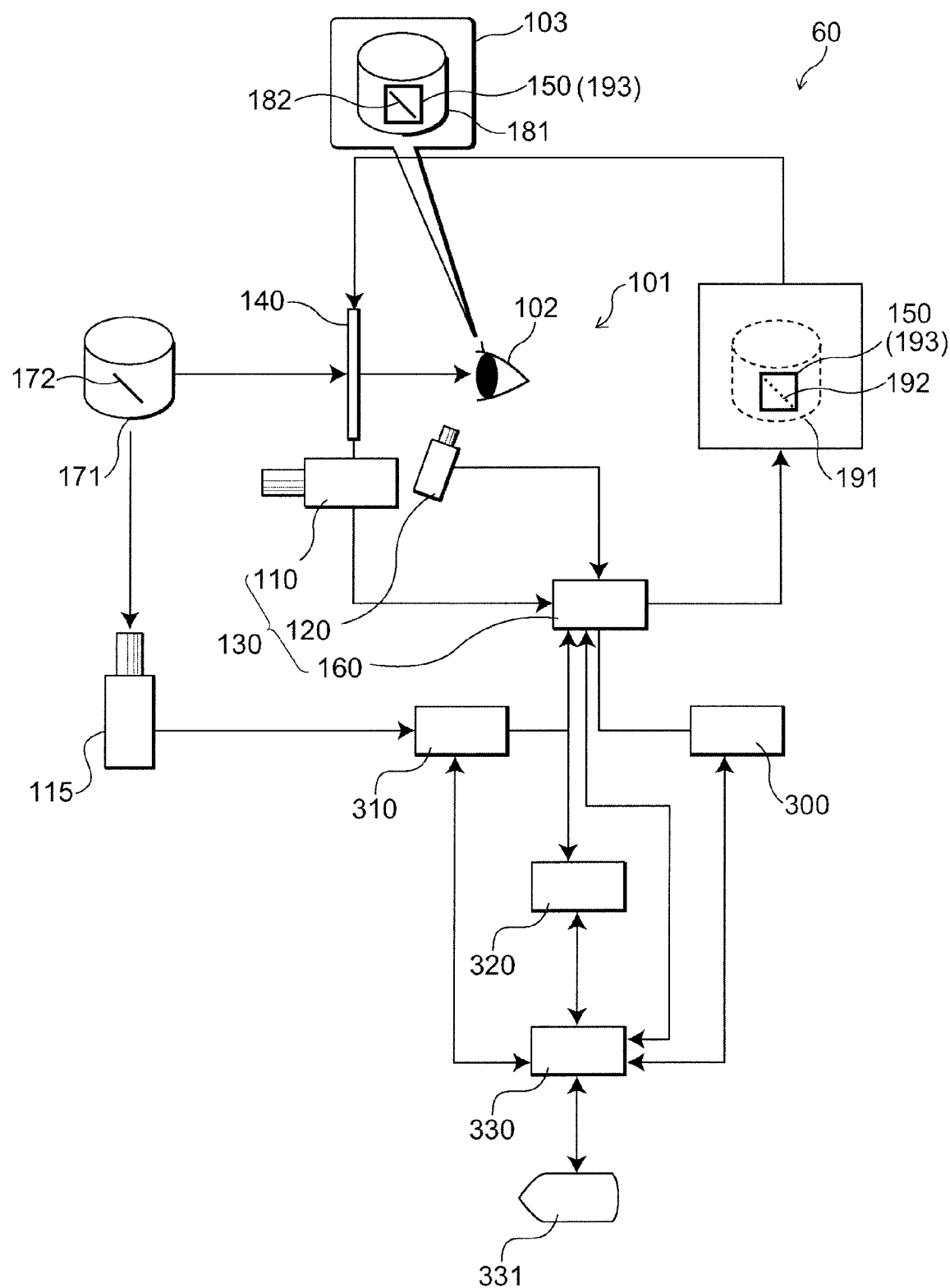
FIG. 10 is a schematic view illustrating the structure of an appearance inspection apparatus according to a six embodiment of the invention.

FIG. 10 is a schematic view illustrating the structure of an appearance inspection apparatus according to a six embodiment of the invention.

As shown in FIG. 10, the appearance inspection apparatus 60 of this embodiment further includes a data analysis section 330 for analyzing the appearance inspection result with respect to the appearance inspection apparatus 40 illustrated in FIG. 6.

Moreover, a display apparatus 331 for displaying the result analyzed by the data analysis section 330 may be further provided. The display apparatus 331 is not necessarily a head mounted display loaded on the head of the inspector 101 but stand-alone CRT, liquid crystal display, organic EL display, and so forth can be used.

The data analysis section 330 analyzes, for example, at least any one of the image inspection result based on an image taken by the image-taking apparatus 115 or an image taken by the image-taking section 110 and the result of visual inspection by the inspector 101. At this time, the inspection data stored in the inspection data storage section 320 can be used.

Moreover, the data analysis section 330 may analyze all of the data relating to the product to be inspected 171 as well as the above-described appearance inspection results. For example, various data such as, data of lot numbers of material or parts used for the product to be inspected 171, for example, which production line the product has been produced by when there are a plurality of production lines, and operators or production time and date, are analyzed. That is, the data analysis section 330 can perform the process history analysis of the product to be inspected 171 as exemplified as follows. The data to be analyzed can be stored in the inspection data storage section 320.

For example, there are a plurality of kinds of products in which a material is used, and in this case, occasionally, a specific error is easily generated in a specific kind of the product. For example, suppose that a resin material is used in a portable phone case according to the lot and phenomena that the case is easily damaged. In this case, occasionally, the dent does not outstand in one model of the portable phone but the dent easily outstands in another mode thereof. In this case, when the material lot is used and the appearance inspection of the combination of the model in which the dent easily outstands, the inspector 101 can be informed of the information. For example, when the inspector 101 performs the appearance inspection, the display for promoting the heavy inspection for the "dent" in the various inspection items can be performed in the display 140.

Moreover, for example, in the production process of the product to be inspected 171, in such a case as each of a plurality of processes has a plurality of processing apparatuses, occasionally, a generation ratio of error of the product produced by combination of a specific processing apparatus of the previous process and a specific apparatus of the post-process is particularly high. And, in such a case, for example, when the inspector 101 inspects the product lot of the combination, the inspector 101 can be informed of the particularly high generation ratio of error in the combination lot. And, in this case, the inspector 101 can also be informed of the error item having the high generation ratio.

By contrast, when it is found that the error ratio in a specific combination of the processing apparatuses is very low, by informing the inspector 101 of the information, the inspection by the inspector 101 can be efficiently performed.

As described above, the data analysis section 330 can perform the history analysis according to the product to be inspected 171, and the inspector 101 can be informed of the analysis, and the efficiency of the appearance inspection by the inspector 101 can be improved. Furthermore, all of the concerned persons such as operators or supervisors of the respective processes according to the production of the product to be inspected 171 or persons responsible for purchasing members can be informed of the information and the efficiency relating to the production of the product to be inspected 171 can be further improved.

For the above, the enhancement of efficiency of the appearance inspection by the method in which the inspector 101 is informed of the analysis result of the data by the data analysis section 330 has been explained, but the analysis result of the data may be feed-backed to the image inspection based on the image taken by the image-taking apparatus 115 or the image taken by the image-taking section 110. For example, by changing the determination criteria (slice level) in the image inspection according to the product to be inspected 171 having a high error generation ratio and the product to be inspected 171 having a low error generation ratio, the efficiency of the image inspection such as time shortening of the image inspection can be improved.

Fourth Example

Figure 11A:
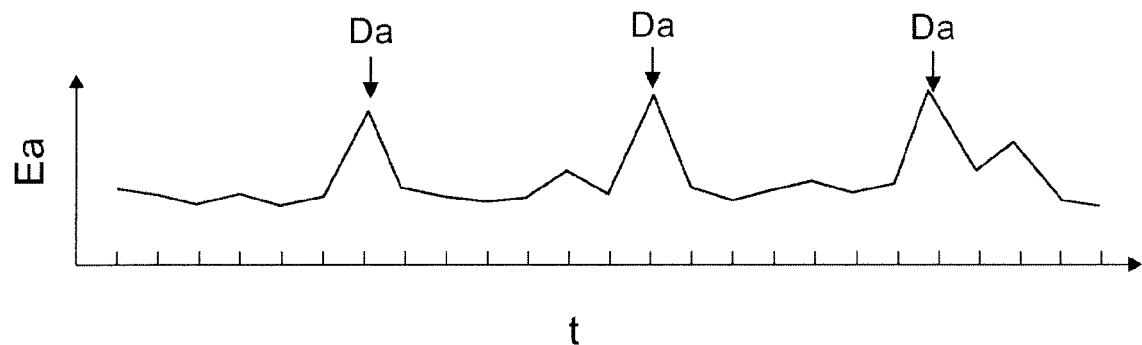
FIGS. 11A and 11B are schematic views illustrating operation of an appearance inspection apparatus according to a fourth example of the invention.
Figure 11B:
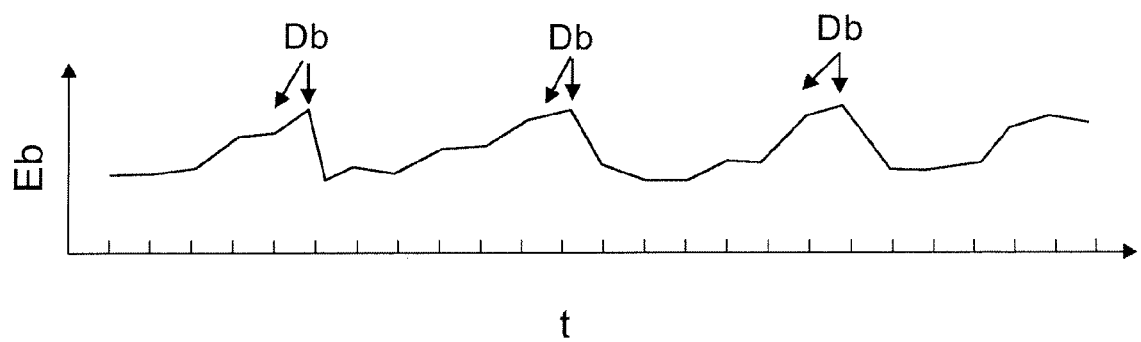

FIGS. 11A and 11B are schematic views illustrating the operation of an appearance inspection apparatus according to a fourth example of the invention. That is, this figure shows one example of the operation of the data analysis section 330 in an appearance inspection apparatus 60, and the FIGS. 11A and 11B represent an error ratio Ea and an error ratio Eb for the error item A and the error item B, respectively. And, the horizontal axes of the FIGS. 11A and 11B represent time t, and represents date in this example. And, the vertical axes of FIGS. 11A and 11B represent the error ratio Ea and the error ratio Eb. That is, this is one example of the result of process history analysis.

As shown in FIG. 11A, the error ratio Ea of the error item A indicates specifically high values in the dates Da every seven days. For example, as described above, the production pattern of the product to be inspected 171 is changed in the period of seven days, and the error ratio Ea is changed in the period of seven days in conjunction with the period.

On the other hand, as shown in FIG. 11B, the error ratio Eb of the error item B indicates change of the period of seven days, and does not indicate high values in a specific days, but the error ratio Eb repeats the change of rising gradually day by day and lowering at the eighth day, in the period of seven days. And, the error ratio in the dates Db is relatively high.

When the error ratio Ea and the error ratio Eb are changed in such a manner, for example, in the appearance inspection in the day corresponding to the date Da, the inspector 101 can be informed of the heavy inspection of the error item A. Moreover, for example, in the appearance inspection of the day corresponding to the date Db, the inspector 101 can be informed of heavy inspection of the error item B. As described above, the efficiency of the appearance inspection can be improved.

In this case, as the method of informing the above-described result, for example, as described later, a method of displaying the result in the display 140 while the inspector 101 is inspecting the product to be inspected 171. Moreover, in the structure, the result is displayed in the display apparatus 331 so that the inspector 101 can see the information before inspecting the product to be inspected 171 or with performing the inspection. Moreover, display of the result does not necessarily act on the visual sense but can inform the information based on the above-described analysis result by a method in which sound or vibration or the like is used.

In the data analysis section 330, from each of the values of the error ratios, it can be analyzed that such a tendency as described above is indicated. For example, the interval between dates in which the local maximum values of each value of the error ratios appear can be calculated, or the interval between emergences of the dates in which the error ratio is a predetermined value or more can be calculated, or the range of the dates of continuously rising or lowering can be calculated, or various methods can be adopted.

Moreover, when there are a plurality of error items, an extent of correspondence between the tendencies that the error items have can also be calculated. Thereby, it can be analyzed that when a specific error is generated, another error is generated at the same time. Moreover, by contrast, it can be analyzed that when a specific error is generated another error is difficult to be generated, that is, these error items are trade-off. Thereby, not only the efficiency of the inspection can be improved but also the efficiency of the improvement of the production process of the product to be inspected 171 can be improved.

Fifth Example

Figure 12:
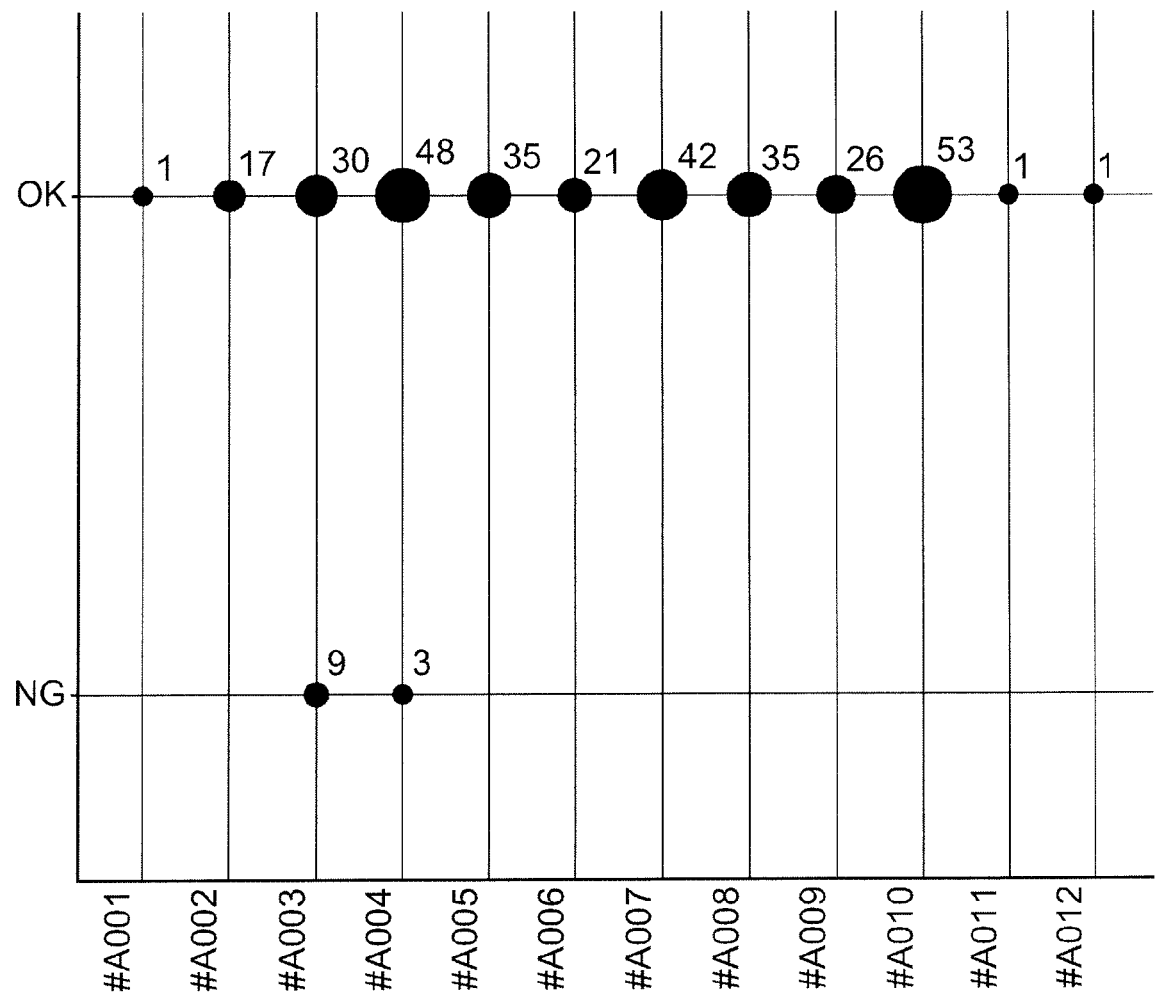
FIG. 12 is a schematic view illustrating operation of an appearance inspection apparatus according to a fifth example of the invention.

FIG. 12 is a schematic view illustrating the operation of an appearance inspection apparatus according to a fifth example of the invention. That is, this figure shows another example of operation of the data analysis section 330 in the appearance inspection apparatus 60. That is, this is one example of the result of the process history analysis. In the specific example, in the production process of the product to be inspected 171, as the production apparatus, twelve production apparatuses #A001 to #A012 are used, and the horizontal axis of this figure corresponds to the number specifying the production apparatus, and the vertical axis corresponds to acceptance (OK) or error (NG) of the appearance result. The size of circle existing in each of the intersections of the line corresponding to the number of each of the production apparatuses and the line of OK or NG corresponds to the number of the product to be inspected 171 produced by the production apparatus. And, the number inscribed above the circle represents the number of OK or NG. The error item in this case is "Error 1" EI1 illustrated in FIG. 9.

As shown in FIG. 12, one product to be inspected 171 was produced by the production apparatus #A001 and the one was non-defective. Moreover, 39 products to be inspected 171 were produced by the production apparatus #A003, and among them, 30 products were non-defective and 9 products were defective. Moreover, in the production apparatus #A010, 53 products to be inspected were produced, and all of them were non-defective.

In the data analysis section 330, for example, the result of the appearance inspection is analyzed. And, the analysis result can be displayed in the display apparatus 331.

Furthermore, for example, in the case of such inspection results, it is analyzed that errors are relatively easily generated in the products to be inspected 171 produced by the production apparatus #A003 and the production apparatus #A004, and errors are relatively difficult to be generated in the products to be inspected 171 produced by the production apparatus #A008 and the production apparatus #A010. And, the inspector 101 can be informed of this information. That is, when the products to be inspected 171 produced by the production apparatus #A003 and the production apparatus #A004 are inspected, it can be promoted to heavily carry out the appearance inspection. Thereby, the efficiency of the appearance inspection is improved.

Also, in this case, various methods such as, a method of displaying the promotion in the display section 140 in the appearance inspection, a method of displaying the promotion in the display apparatus 331, and a method by sound or vibration or the like can be used.

Sixth Example

Figure 13:
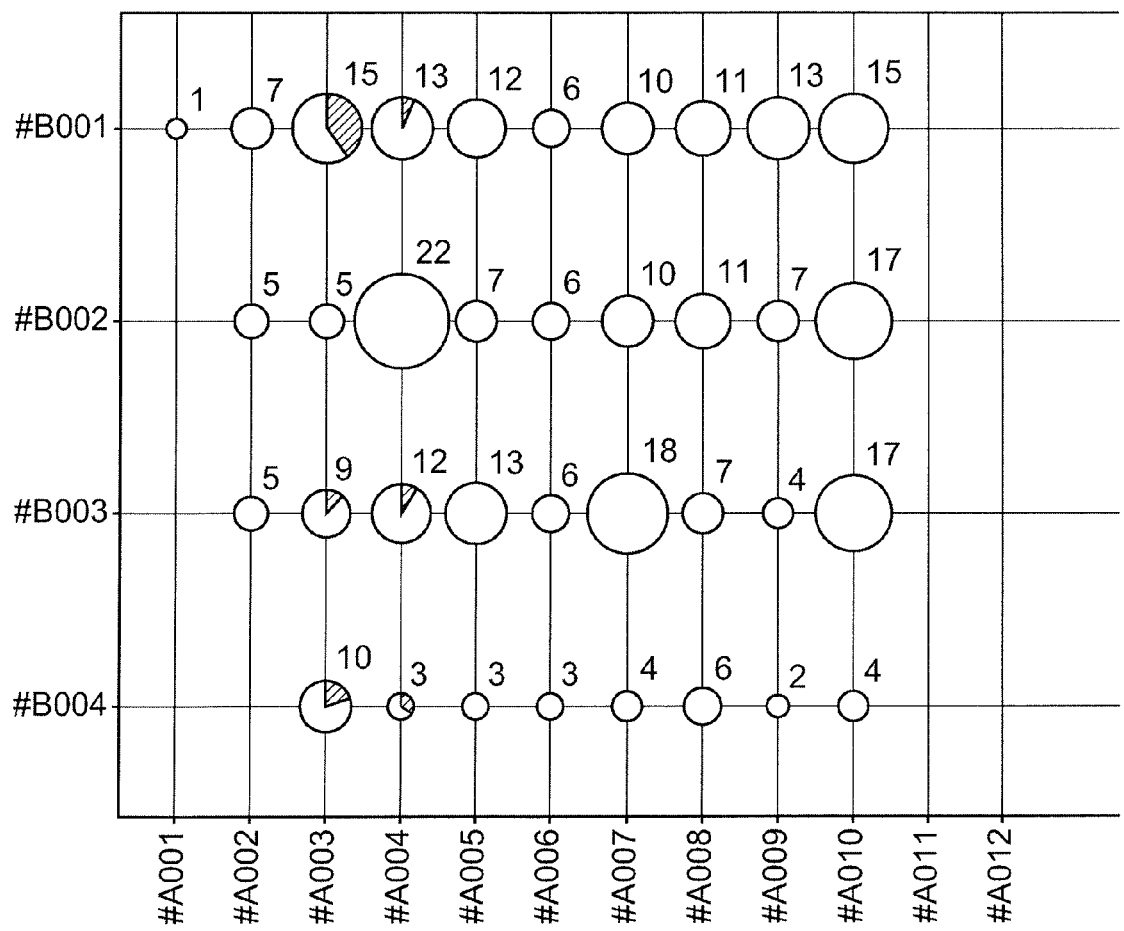
FIG. 13 is a schematic view illustrating operation of an appearance inspection apparatus according to a sixth example of the invention.

FIG. 13 is a schematic view illustrating the operation of an appearance inspection apparatus according to a sixth example of the invention. That is, this figure shows further another example of operation of the data analysis section 330 in the appearance inspection apparatus 60. That is, this is one example of the result of the process history analysis. In the specific example, the production process of the product to be inspected 171 has Step 1 and Step 2, and in Step 1, 10 production apparatuses #A001 to #A010 are used, and in Step 2, four production apparatuses #B001 to #B004 are used. The horizontal axis of this figure corresponds to the number specifying the production apparatus of Step 1, and the vertical axis corresponds to the number specifying the production apparatus of Step 2.

And, the size of circle existing in each of the intersections of the lines corresponding to the numbers of the respective production apparatuses and the number inscribed above the circle represents the number of the products to be inspected 171 produced by the combination of the production apparatuses. And, the part to which diagonal lines are appended represents the ratio of the number of the appearance error out of the number of the products produced by the combination of the production apparatuses, namely, the error ratio. That is, the part to which the diagonal lines are not appended represented the non-defective ratio.

As shown in FIG. 13, it is analyzed that the error ratio is high in the products to be inspected 171 produced by using the production apparatus #A003 and the production apparatus #A004 of Step 1. Furthermore, it is analyzed that when the production apparatus #A003 or the production apparatus #A004 is used and the production apparatus #B001 or the production apparatus #B003 or the production apparatus #B004 is used, the error ratio is particularly high. Such analysis is performed in the data analysis section 330.

And, the inspector 101 can be informed of the above-described analysis result. That is, when the product to be inspected 171 produced by using the production apparatus #A003 or the production apparatus #A004 and the production apparatus #B001 or the production apparatus #B003 or the production apparatus #B004 is inspected, it can be promoted to heavily carry out the appearance inspection. Thereby, the efficiency of the appearance inspection is improved.

Also, in this case, various methods such as, a method of displaying the promotion in the display section 140 in the appearance inspection, a method of displaying the promotion in the display apparatus 331, and a method by sound or vibration or the like can be used.

Of the analysis result explained in the above-described fourth to sixth examples, not only the inspector 101 is informed but also all of the concerned persons such as operators or supervisors of the respective processes according to the production of the product to be inspected 171 or persons responsible for purchasing members can be informed, and the efficiency relating to the production of the product to be inspected 171 can be further improved.

Seventh Example

Figure 14A:
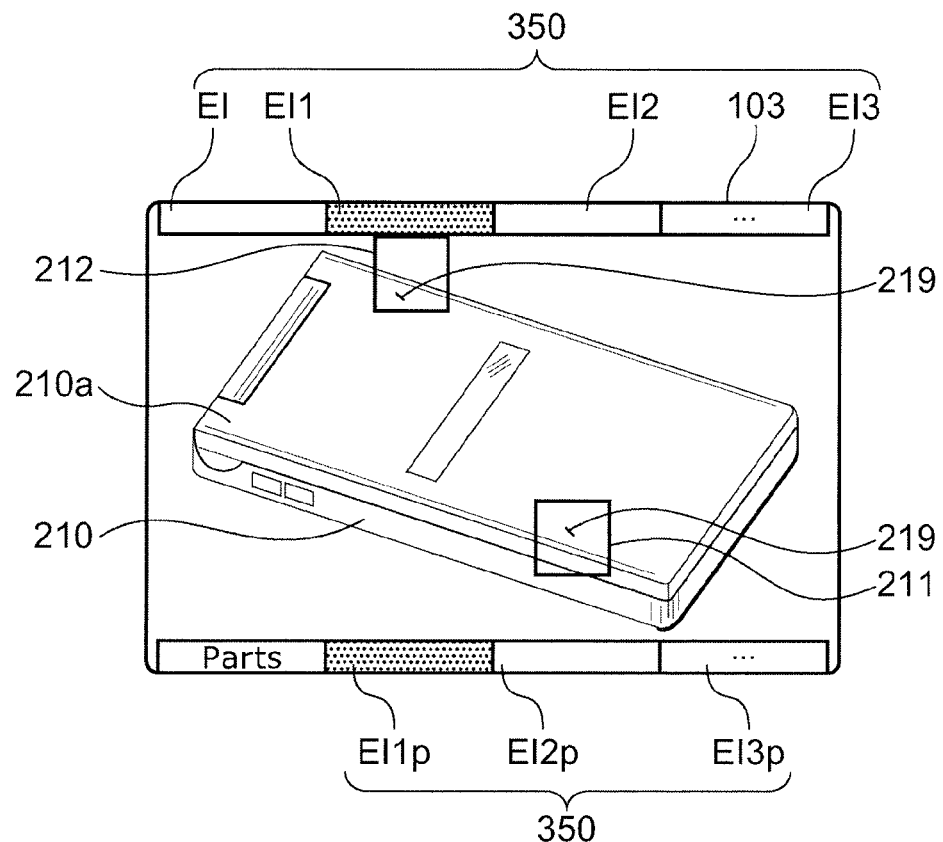
FIGS. 14A and 14B are schematic views illustrating operation of an appearance inspection apparatus according to a seventh example of the invention.
Figure 14B:
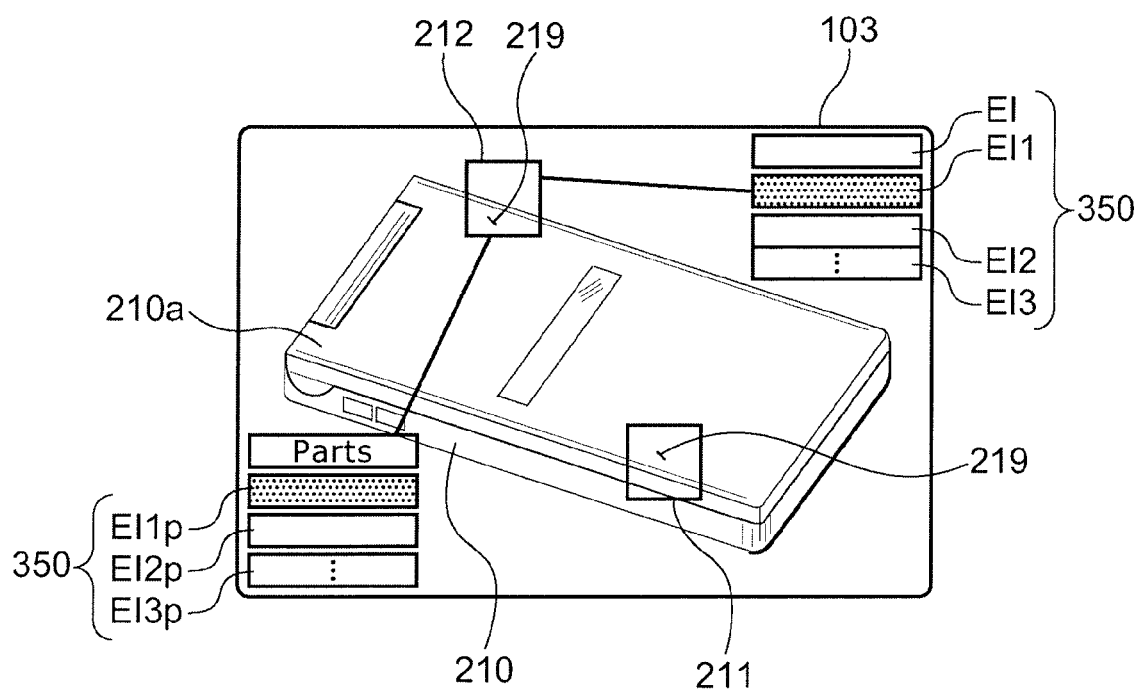

FIGS. 14A and 14B are schematic views illustrating the operation of an appearance inspection apparatus according to a seventh example of the invention. That is, the figures show one example of technique for informing the inspector 101 of the analysis result by the data analysis section 330 in the appearance inspection apparatus 60. Here, as one example, the case in which the head mounted display loaded on the head of the inspector 101 is adopted as the display 140 will be explained. And, the figures are examples in which the information based on the analysis result of the above-described data analysis section 330 is displayed in the visual field 103 of the inspector 101 illustrated in FIG. 3. FIG. 14A is one example thereof, and FIG. 14B is another example.

As shown in FIG. 14A, in the visual field 103 of the inspector 101, the portable phone 210 (picture 210a) of the product to be inspected 171 that is the image 181 of observation by the inspector 101 is shown up. And, as described previously, as the image inspection result 150, quadrangular frames 211 and 212 representing the generation position of defects are displayed. And, thereby, the dent 219 is displayed. As described previously, the above-described image inspection result 150 can be the inspection result based on the image taken by at least any one of the image-taking section 110 and the image-taking apparatus 115.

And, further, in this example, in the display 140, information 350 based on the analysis result of the data analysis section 330 is displayed. In this specific example, as the "Error 1" EI1 of the error items (error categories) EI, "scratch" is displayed, and as "Error 2" EI2 thereof, "dint" is displayed. Moreover, as "Error 1 parts" EI1p, "liquid crystal panel" is displayed, and as "Error 2 parts" EI2p, "hinge" is displayed.

At this time, for the display of "scratch" that is the "error 1" EI1, hatching or coloring is performed, and also, for the display of "liquid crystal panel" that is the "Error 1 parts" EI1p, hatching or coloring is performed.

That is, in this specific example, by the data analysis section 330, it was analyzed that "scratch" is easily generated in a part of "liquid crystal panel" in the product to be inspected 171 that is being inspected now. In this example, the result is being displayed in the visual field 103 of the inspector 101 by the display 140.

Thereby, the inspector 101 can heavily perform the appearance inspection for the "scratch" of the part of "liquid crystal panel". Thereby, the efficiency of the appearance inspection can be improved and generation of miss of error or missdetection can be suppressed.

In the specific example illustrated in FIG. 14A, the information 350 based on the analysis result of the data analysis section 330 was displayed in the position fixed in the lower portion of the upper part of the display screen, but in the following another specific example, the position in which the information 350 is displayed is changed according to the contents thereof.

That is, as shown in FIG. 14B, for example, when it was analyzed that the "scratch" is easily generated in the part of "liquid crystal panel" that is one of the parts, by a leading line drawn from the position corresponding to the "liquid crystal panel", "liquid crystal panel" is displayed. And, by the leading line drawn from the part in which the "scratch" is generated, it is displayed that the content of the error is "scratch". Thereby, the inspector 101 can more easily recognize what error is easily generated in what place. Thereby, the efficiency of the appearance inspection is more improved.

In FIGS. 14A and 14B, in these structures, the respective items of the error items (error categories) EI are displayed, for example, in three frames such as "scratch" and "dint", and the corresponding item(s) out of them is/are further displayed by hatching or coloring, but only the corresponding item(s) may be displayed. Moreover, in the same manner, in these structures, the respective items of "error 1 parts" are displayed, for example, in three frames such as "liquid crystal panel" and "hinge", and the corresponding item(s) out of them is/are further displayed by hatching or coloring, but only the corresponding item(s) may be displayed. Thereby, the display becomes easily viewable.

Seventh Embodiment

Figure 15:
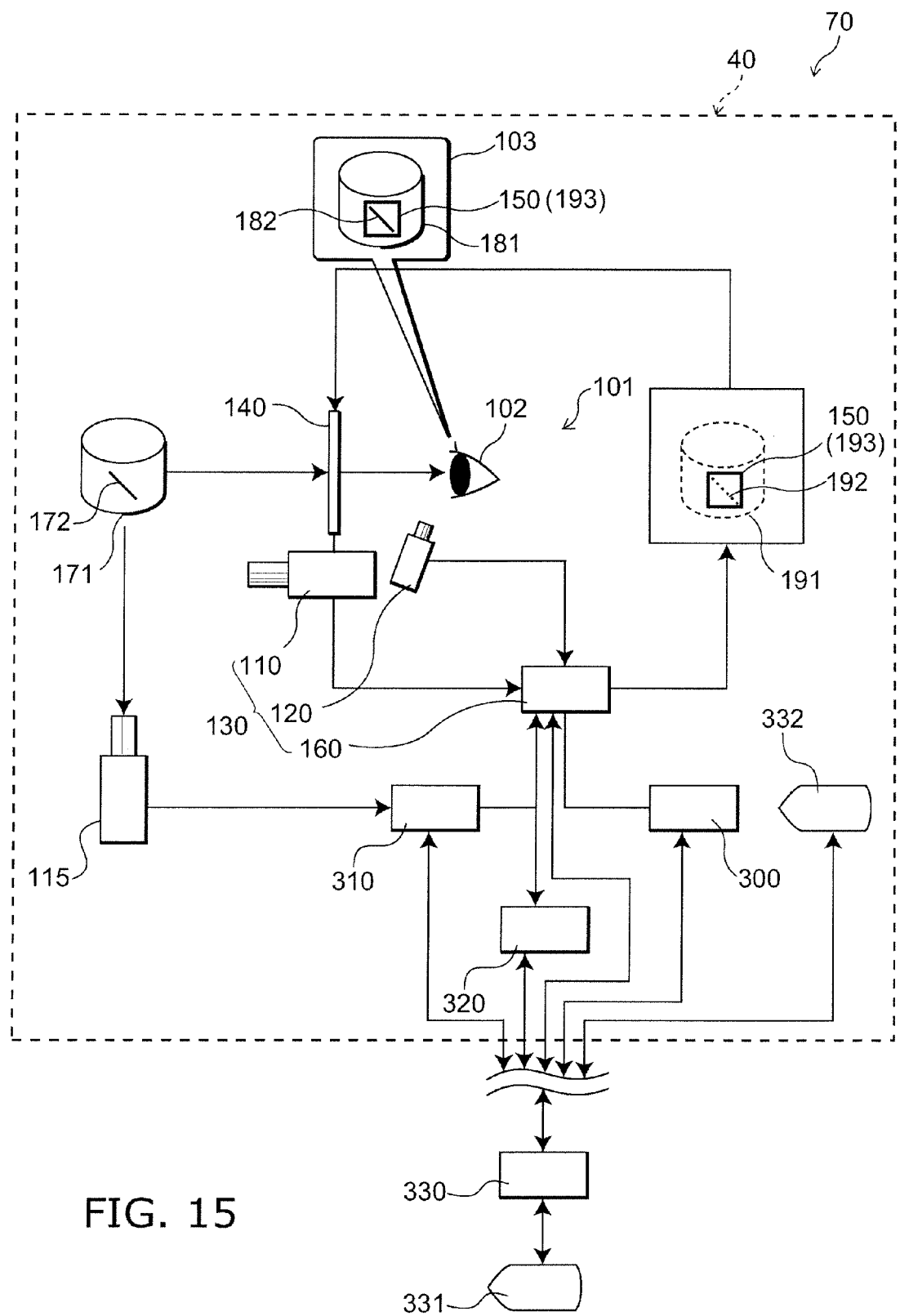
FIG. 15 is a schematic view illustrating an appearance inspection system according to a seventh embodiment of the invention.

FIG. 15 is a schematic view illustrating an appearance inspection system according to a seventh embodiment of the invention.

As shown in FIG. 15, in the appearance inspection system 70 according to this embodiment, with respect to the appearance inspection apparatus 40 illustrated in FIG. 6, the data analysis section 330 for analyzing the appearance inspection result is further provided. And, in this example, the data analysis section 330 is placed in the place separate from the place in which the inspector 101 performs the appearance inspection.

That is, the appearance inspection system 70 further includes the data analysis section 330 for receiving the result of the appearance inspection of the product to be inspected 171 by the inspector 101 through the communication system from the appearance inspection apparatus 40 and analyzing the result.

The data analysis section 330 in the present embodiment can perform the process history analysis of the product to be inspected 171 as described previously. In addition, the operation of the data analysis section 330 in this embodiment can be the same as the operation of the data analysis section 330 in the sixth embodiment, and therefore, the explanation thereof will be omitted.

In the case that the data analysis section 330 is placed separately from the place in which the appearance inspection is performed in such a manner as the appearance inspection system 70 according to this embodiment, transmission and reception of data between the visual-inspection-result inputting section 300, the image-inspection-treating section 310, the inspection data storage section 320 and image-treating section 160, and the data analysis section 330 can be carried out by using communication system such as electrical communication pathway or optical communication pathway such as local area network or internet.

In the appearance inspection apparatus 60, the data analysis section 330 is provided as one part of the appearance inspection apparatus 60, and for example, the data analysis section 330 is provided near the place in which the appearance inspection is performed. However, in the appearance inspection system 70 according to this embodiment, the data analysis section 330 can be placed in an optional place, and the appearance inspection system that is more convenient and has a high general versatility can be provided.

In the appearance inspection system 70, for example, the information 350 based on the analysis result of the data analysis section 330 can also be displayed in the display 140 used by the inspector 101, and also can be displayed in the display apparatus 332 used by the inspector 101. In this case, by using a method for applying an electrical communication technique such as e-mail, the efficiency is enhanced. And, of the information 350 based on the analysis result of the data analysis section 330, not only the display apparatus 332 viewed by the inspector 101 but also all of the concerned persons such as the administrator of the inspector or operators or supervisors of the respective processes according to the production of the product to be inspected 171 or persons responsible for purchase can be efficiently informed, and the efficiency relating to the production of the product to be inspected 171 can be further improved.

In this specific example, the data analysis section 330 and the display apparatus 331 attached thereto are provided separately from the appearance inspection apparatus 40. The invention is not limited thereto. For example, the image data storage section 320 attached to the appearance inspection apparatus 40 may be separated from the appearance inspection apparatus 40, and transmission and reception of the mutual data may be performed between the inspection data storage section and the appearance inspection apparatus by using electrical communication pathway or optical communication pathway or the like, as well as the data analysis section 330.

That is, the appearance inspection system 70 according to this embodiment can further includes an inspection data storage section 320 for receiving the result of the appearance inspection of the product to be inspected 171 by the inspector 101 through a communication system from the appearance inspection apparatus and storing the result. And, the inspection data storage section 320 stores the result in association with the information specifying the product to be inspected 171 (such as lot number). And, the inspection data storage section 320 can automatically collect and store the result. Thereby, efficiency of the collection of the data is improved.

Similarly, in this structure, another part that can be attached to the appearance inspection apparatus is removed and the transmission and reception of the data can also be performed between the part and the appearance inspection apparatus through a communication system. For example, the image-taking apparatus 115 or the image-treating section 160 in the observation-image-cognizing section 130 may be composed in such a manner.

By the appearance inspection system 70 according to this embodiment, the appearance inspection system by which the results of the image inspection and the visual inspection can be easily referred and the appearance inspection of high accuracy can be performed with high efficiency can be provided.

Eighth Embodiment

Next, an appearance inspection method of an eighth embodiment of the invention will be explained.

Figure 16:
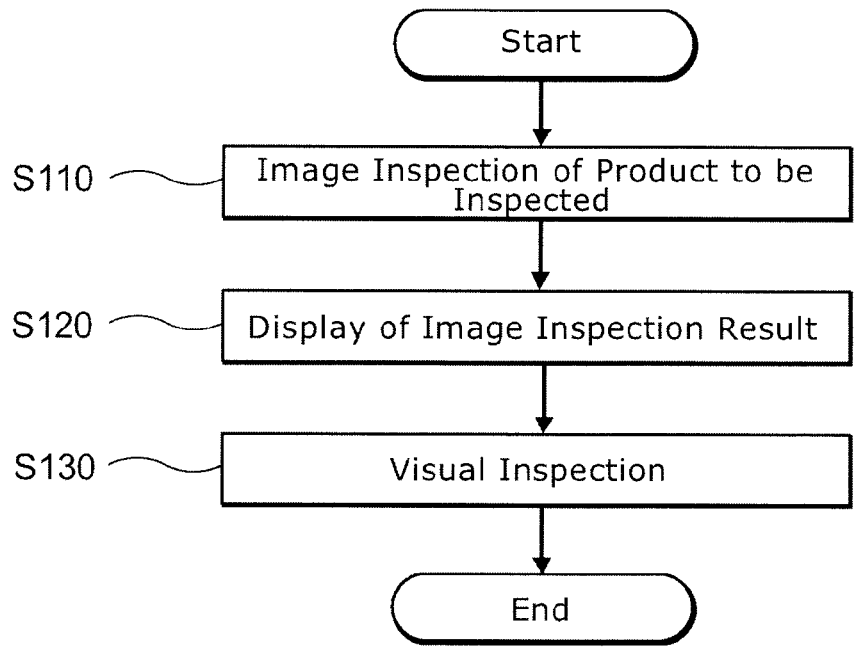
FIG. 16 is a flow chart illustrating an appearance inspection method according to an eighth embodiment of the invention.

FIG. 16 is a flow chart illustrating the appearance inspection method according to the eighth embodiment of the invention.

As shown in FIG. 16, in the appearance inspection method according to the eighth embodiment, first, the product to be inspected 171 is image-inspected based on the result of image-taking the product to be inspected 171 (Step S110). For this, for example, the image-taking section 110 illustrated in FIG. 1 or the image-taking apparatus 115 except therefor can be used. In the case of using the image-taking section 110, the taken image can be image-treated in the image-treating section 160.

Next, the image inspection result 150 is superposed on the visual field of the inspector 101 inspecting the product to be inspected 171 and displayed in the position corresponding to the image 181 of the product to be inspected 171 which the inspector 101 observes (Step S120). This display can be performed by, for example, the display 140 illustrated in FIG. 1. Moreover, for this, the image 191 of the product to be inspected 171 image-taken by the image-taking section 110 is used. And, the visual line of the inspector 101 is detected by the visual line detection section 120, and from the direction of the visual line, the image 181 being observed by the inspector 101 is obtained, and the result of performing the image treatment by the image-treating section 160 based thereon can be used. For the display, the above-described frame 193 or the like can be used.

And, the inspector 101 inspects the product to be inspected 171 with eyes (Step 130).

Thereby, the inspector 101 can easily refer the image inspection result 150 with performing the visual inspection, and the appearance inspection of high accuracy can be performed with high efficiency.

In the above, the order of Step S110 to Step S130 is optional, and the steps can be carried out at the same time, and also, all or a part of these steps can be carried out with repeated.

Ninth Embodiment

Next, an appearance inspection method of a ninth embodiment of the invention will be explained.

Figure 17:
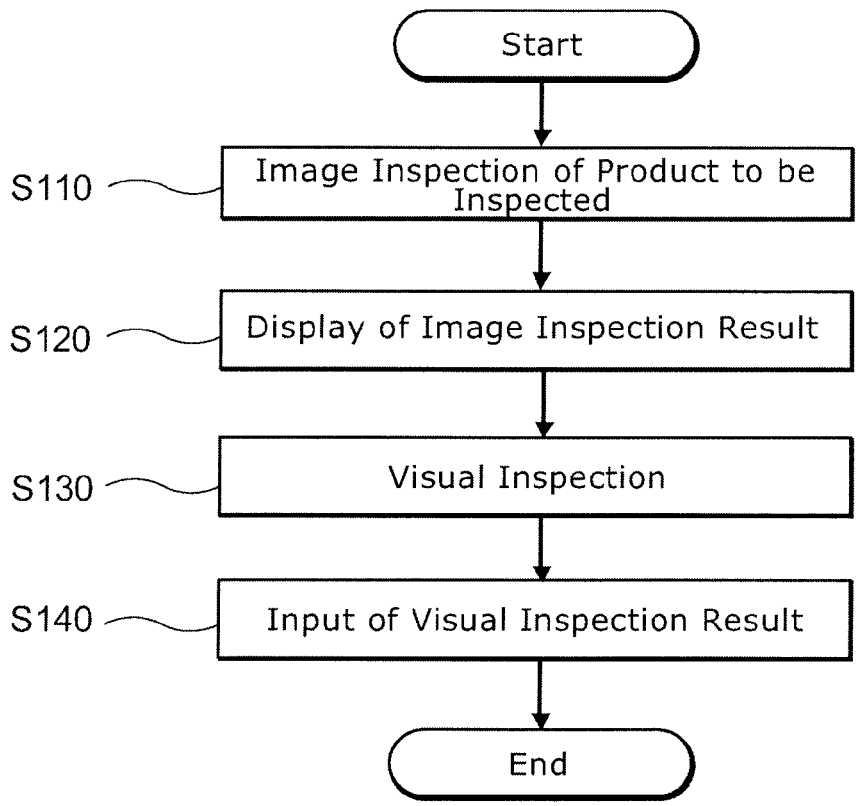
FIG. 17 is a flow chart illustrating an appearance inspection method according to a ninth embodiment of the invention.

FIG. 17 is a flow chart illustrating the appearance inspection method according to the ninth embodiment of the invention.

As shown in FIG. 17, in the appearance inspection method according to the ninth embodiment, with respect to the appearance inspection method of the eighth embodiment illustrated in FIG. 16, the input of the visual inspection result is further performed. (Step S140). Thereby, the appearance inspection can be performed efficiently, and the result of the appearance inspection can be stored and utilized, and thereby, the appearance inspection of high accuracy can be performed with high efficiency.

Tenth Embodiment

Next, an appearance inspection method of a tenth embodiment of the invention will be explained. In the appearance inspection method of this embodiment, the display is performed by changing the display state of the image inspection result 150 based on the time in which the inspector 101 observes a predetermined part of the product to be inspected 171. Moreover, in this example, based on the image obtained by the image-taking section 110, the image inspection of the product to be inspected 171 is performed.

Figure 18:
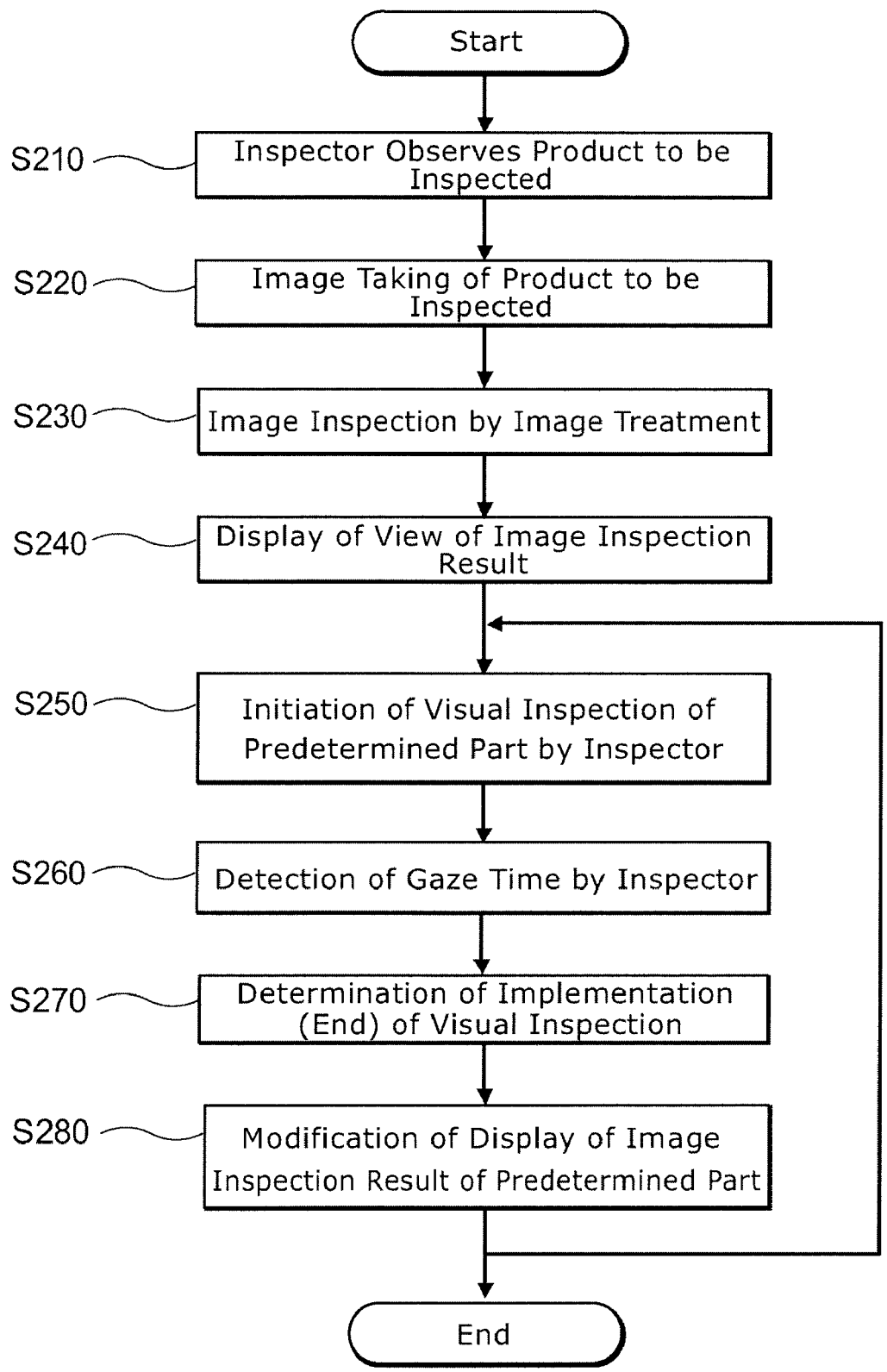
FIG. 18 is a flow chart illustrating an appearance inspection method according to a tenth embodiment of the invention.

FIG. 18 is a flow chart illustrating the appearance inspection method according to the tenth embodiment of the invention.

As shown in FIG. 18, in the appearance inspection method according to the tenth embodiment of the invention, first the inspector 101 observes the product to be inspected 171 (Step S210). This observation is in the state before performing detailed visual inspection, and for example, the rough state of the product to be inspected 171 is being observed, and in this state, the visual inspection of global appearance is being performed.

Next, the product to be inspected 171 is image-taken by the image-taking section 110 (Step S220).

And, the taken image is image-treated and the image inspection is performed (Step S230).

And, the view of the obtained image inspection result 150 is superposed on the visual field of the inspector 101 observing the product to be inspected 171, and displayed in the position corresponding to the image 181 of the product to be inspected 171 observed by the inspector 101 (Step S240). In this case, when a plurality of defects have been found in the product to be inspected 171 by the image inspection, the positions of all of the defects can be displayed by the frames 193 or the like. Thereby, the inspector 101 can take a look at and recognize the image inspection results 150 of the product to be inspected 171. In this case, it is also possible that the positions of all of the defects are not shown but, for example, the frames are sequentially displayed in the appropriate order for the visual inspection and thereby the next frame is displayed after each of the visual inspections of the defects of the respective frames is finished.

And, the inspector 101 starts the visual inspection of any one of the plurality of defects (a predetermined part in any one of the frames) (Step 250).

In this case, the visual line of the inspector 101 is constantly detected by the visual-line-detecting section 120, and the time of gazing at the inside of the predetermined part by the inspector 101 is measured and the gaze time is detected (Step S260).

And, for example, when the time of gazing at the predetermined part exceeds the preliminarily determined time or the accumulation time or the number of gazing at the predetermined part satisfy the preliminarily determined condition, it is determined that the visual inspection is initiated or being carried out or finished (Step 270).

And, when it is determined that the visual inspection is initiated or being carried out or finished, the display (frame 193) of the predetermined image inspection result 150 is changed. For example, the frame 193 is vanished or the color of the frame 193 is modified (Step S280).

And, thereby, when the visual inspection of the predetermined part is finished, by returning to Step S250, the visual inspection of the part of another defect is performed.

Thereby, the inspector 101 does not repeatedly inspect the place of the same defect, and does not miss an inspection place, and can easily and efficiently refer the image inspection result with performing the visual inspection and the appearance inspection of high accuracy can be performed with high efficiency.

In the above, in the case of one defect, the repeat of Step S250 to Step S280 is not performed, and these steps are carried out only at one time.

Moreover, in the above-described example, the image inspection is performed by the image-taking section 110, but when the image inspection is performed by another image-taking apparatus, Steps S220 to S230 may be omitted or performed independently.

In the above, the order of Step S210 to Step S280 may be interchanged in the technically possible range or the steps may be carried out at the same time. Furthermore, a part thereof may be omitted or modified. Moreover, all or a part of these steps can be repeatedly carried out. In particular, the steps S210 to S240 can be performed at the same time. Moreover, Steps S250 and S260 can be performed at the same time.

Eleventh Embodiment

Next, an appearance inspection method of an eleventh embodiment of the invention will be explained.

Figure 19:
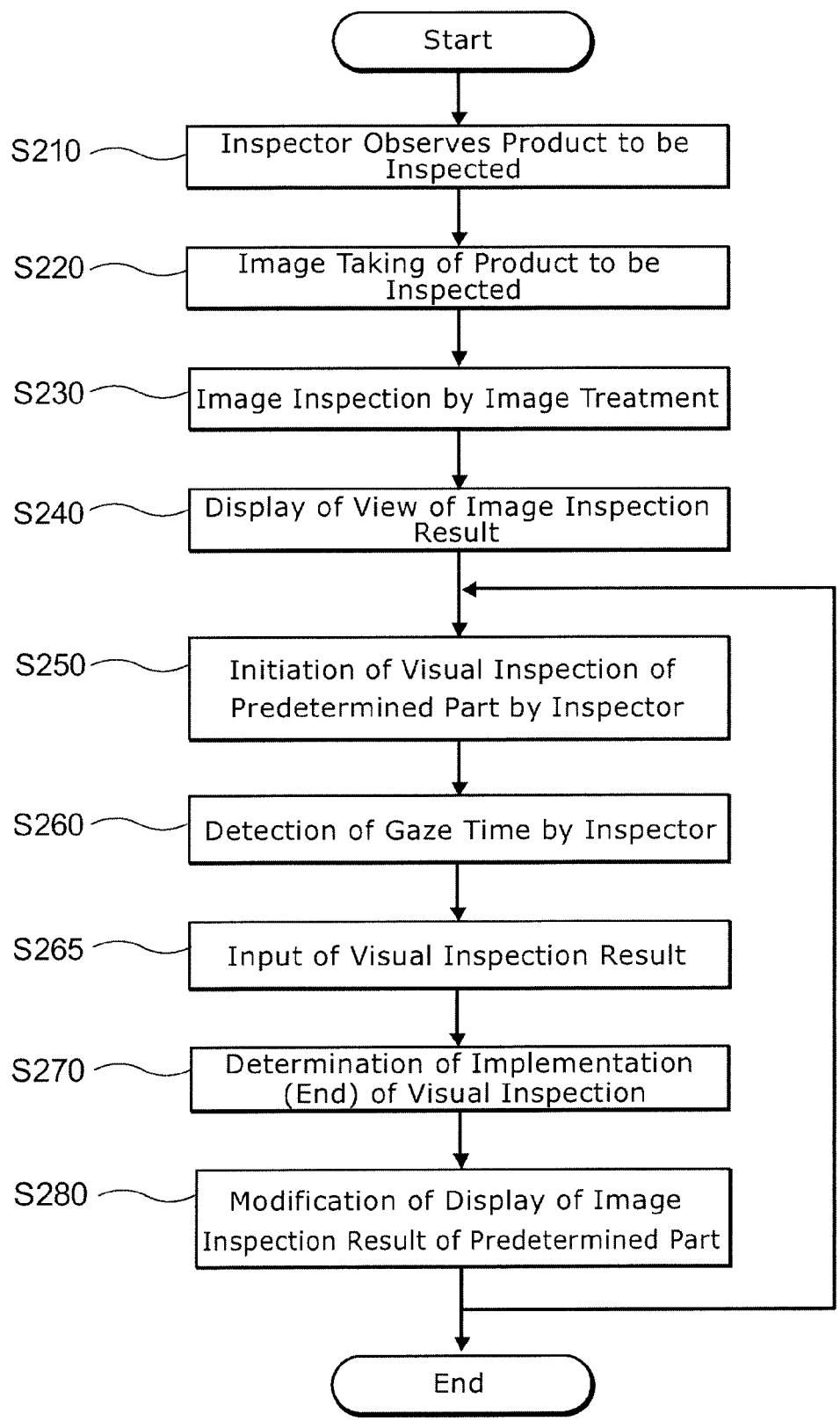
FIG. 19 is a flow chart illustrating an appearance inspection method according to an eleventh embodiment of the invention.

FIG. 19 is a flow chart illustrating the appearance inspection method according to the eleventh embodiment of the invention.

As shown in FIG. 19, in the appearance inspection method according to the eleventh embodiment, with respect to the appearance inspection method of the tenth embodiment illustrated in FIG. 18, the input of the visual inspection result is further performed (Step S265). Thereby, the appearance inspection can be efficiently performed, and the result of the appearance inspection is stored and utilized, thereby, the appearance inspection of high accuracy can be performed with high efficiency.

The order of the input of the visual inspection result of Step S265 and other Steps S260 to S280 is optional.

Moreover, the display of, for example, the frame representing the image inspection result 150 may be changed according to whether the input of the visual inspection result is not carried out yet or is already carried out. Thereby, the efficiency of the visual inspection is enhanced.

The appearance inspection apparatus and the appearance inspection method of the embodiment of the invention can be used for the inspection of appearance of various products or appearance of parts thereof. Moreover, for example, they are applicable to various inspections such as, inspection of unevenness or dent of display, inspection of paint unevenness, and inspection of unevenness or foreign matter in, for example, extrusion of various films.

As described above, the embodiments of the invention have been explained. However, the invention is not limited to these specific examples. For example, the specific structures of each of components composing the appearance inspection apparatus, the appearance inspection system, and the appearance inspection method are included in the scope of the invention as long as the invention can be carried out in the same manner by appropriate selection from the known range by those skilled in the art and the same effect can be obtained.

Moreover, the combination of two or more components of each of the specific examples in the technically possible range is also included in the scope of the invention as long as including the spirit of the invention.

In addition, all of the appearance inspection apparatuses, the appearance inspection systems, and appearance inspection methods that can be carried out with appropriately design-modified by those skilled in the art based on the appearance inspection apparatus, the appearance inspection system, and the appearance inspection method that have been described above as the embodiments of the invention also belong to the scope of the invention as long as including the spirit of the invention.

In addition, it is understood that those skilled in the art can achieve various change examples and modification examples in the range of the idea of the invention and that the change examples and the modification examples also belong to the scope of the invention.

The invention claimed is:

1. An appearance inspection apparatus, wherein an image inspection result based on a result of image-taking and image-analyzing a product to be inspected can be displayed with superposed on a visual field of an inspector inspecting the product to be inspected with an eye and in a position corresponding to an image in which the inspector is observing the product to be inspected, wherein a display of the image inspection result can be changed according to a time in which the inspector observes a specific part of the product to be inspected.

2. The apparatus according to claim 1, wherein a position of a defect detected by the image analysis is displayed with superposed on the visual field of the inspector.

3. The apparatus according to claim 1, further comprising an appearance inspection input section in which a result of appearance inspection of the product to be inspected by the inspector can be input.

4. The apparatus according to claim 1, further comprising an inspection data storage section for storing a result of appearance inspection of the product to be inspected by the inspector therein.

5. The apparatus according to claim 4, wherein the inspection data storage section stores the result in association with information specifying the product to be inspected.

6. The apparatus according to claim 4, wherein the inspection data storage section automatically collects and stores the result.

7. The apparatus according to claim 1, further comprising a data analysis section for analyzing a result of appearance inspection of the product to be inspected by the inspector.

8. The apparatus according to claim 7, wherein the data analysis section performs a process history analysis of the product to be inspected.

9. An appearance inspection apparatus, wherein an image inspection result based on a result of image-taking and image-analyzing a product to be inspected can be displayed with superposed on a visual field of an inspector inspecting the product to be inspected with an eye and in a position corresponding to an image in which the inspector is observing the product to be inspected, wherein the image inspection result can be displayed in a position according to change of a visual line of the inspector.

10. The apparatus according to claim 9, further comprising an appearance inspection input section in which a result of appearance inspection of the product to be inspected by the inspector can be input.

11. The apparatus according to claim 9, further comprising an inspection data storage section for storing a result of appearance inspection of the product to be inspected by the inspector therein.

12. The apparatus according to claim 11, wherein the inspection data storage section stores the result in association with information specifying the product to be inspected.

13. The apparatus according to claim 11, wherein the inspection data storage section automatically collects and stores the result.

14. The apparatus according to claim 9, further comprising a data analysis section for analyzing a result of appearance inspection of the product to be inspected by the inspector.

15. The apparatus according to claim 14, wherein the data analysis section performs a process history analysis of the product to be inspected.

16. The apparatus according to claim 9, wherein a position of a defect detected by the image analysis is displayed with superposed on the visual field of the inspector.

17. An appearance inspection method comprising:
performing image inspection of a product to be inspected by image-taking the product to be inspected and image-analyzing the product to be inspected in an image-treating section,
an inspector being capable of inspecting the product to be inspected with an eye in the state that a result of the image inspection is displayed with superposed on a visual field of an inspector inspecting the product to be inspected with an eye and in a position corresponding to an image in which the inspector is observing the product to be inspected, wherein a display of the image inspection result is changed according to a time in which the inspector observes a specific part of the product to be inspected.

* * * * *